(12) United States Patent
Cohen et al.

(10) Patent No.: US 8,038,699 B2
(45) Date of Patent: Oct. 18, 2011

(54) PERCUTANEOUS INSTRUMENT ASSEMBLY

(75) Inventors: Dan S. Cohen, Miami Beach, FL (US); Nicholas J. Bender, Budd Lake, NJ (US); Oliver Buchert, Wallington, NJ (US); Rui J. Ferreira, Livingston, NJ (US)

(73) Assignee: EBI, LLC, Parsippany, NJ (US)

( * ) Notice: Subject to any disclaimer, the term of this patent is extended or adjusted under 35 U.S.C. 154(b) by 1422 days.

(21) Appl. No.: 11/527,246

(22) Filed: Sep. 26, 2006

(65) Prior Publication Data

US 2008/0125788 A1 May 29, 2008

(51) Int. Cl.
*A61B 17/70* (2006.01)

(52) U.S. Cl. ..................... 606/246

(58) Field of Classification Search .......... 600/233–235; 606/104, 246, 250, 914, 916
See application file for complete search history.

(56) References Cited

U.S. PATENT DOCUMENTS

| | | | |
|---|---|---|---|
| 4,386,603 A | 6/1983 | Mayfield |
| 4,733,657 A | 3/1988 | Kluger |
| 4,926,849 A | 5/1990 | Downey |
| 4,957,495 A | 9/1990 | Kluger |
| 5,219,349 A | 6/1993 | Krag et al. |
| 5,354,292 A | 10/1994 | Braeuer et al. |
| 5,728,046 A | 3/1998 | Mayer et al. |
| 5,785,648 A | 7/1998 | Min |
| 6,123,707 A | 9/2000 | Wagner |
| 6,139,549 A | 10/2000 | Keller |
| 6,159,179 A | 12/2000 | Simonson |
| 6,287,313 B1 | 9/2001 | Sasso |
| 6,530,929 B1 | 3/2003 | Justis et al. |
| 6,562,046 B2 | 5/2003 | Sasso |
| 6,648,888 B1 | 11/2003 | Shluzas |
| 6,723,097 B2 | 4/2004 | Fraser et al. |
| 6,749,613 B1 | 6/2004 | Conchy et al. |
| 6,749,614 B2 | 6/2004 | Teitelbaum et al. |
| 6,764,512 B2 | 7/2004 | Keller |
| 6,821,277 B2 | 11/2004 | Teitelbaum |
| 6,945,933 B2 | 9/2005 | Branch et al. |
| 7,008,422 B2 | 3/2006 | Foley et al. |
| 7,011,660 B2 | 3/2006 | Sherman et al. |
| 7,056,321 B2 | 6/2006 | Pagliuca et al. |

(Continued)

FOREIGN PATENT DOCUMENTS

EP 0553782 8/1993

(Continued)

OTHER PUBLICATIONS

PCT International Search Report for PCT/US2007/020691 dated Apr. 2, 2008.

(Continued)

*Primary Examiner* — Nicholas Woodall
(74) *Attorney, Agent, or Firm* — Harness, Dickey

(57) ABSTRACT

A percutaneous tower for the orthopedic procedures. The tower can include an outer elongated member, an inner elongated member received within the outer elongated member, a release actuator operable to move the inner elongated member relative to the outer elongated member between first and second positions, and a fastener engagement member coupled to a distal portion of the tower and operable to engage a bone fastener when the inner elongated member is in the first position, and to disengage the bone fastener when the inner elongated member is in the second position.

17 Claims, 18 Drawing Sheets

U.S. PATENT DOCUMENTS

| | | |
|---|---|---|
| 7,073,415 B2 | 7/2006 | Casutt et al. |
| 7,160,300 B2 | 1/2007 | Jackson |
| 7,250,052 B2 | 7/2007 | Landry et al. |
| 7,465,306 B2 | 12/2008 | Pond, Jr. et al. |
| 7,470,279 B2 | 12/2008 | Jackson |
| 7,491,218 B2 | 2/2009 | Landry et al. |
| 2002/0161368 A1 | 10/2002 | Foley et al. |
| 2003/0208203 A1 | 11/2003 | Lim et al. |
| 2004/0039384 A1 | 2/2004 | Boehm, Jr. et al. |
| 2004/0092939 A1 | 5/2004 | Freid et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0158258 A1* | 8/2004 | Bonati et al. ............ 606/104 |
| 2004/0172022 A1 | 9/2004 | Landry et al. |
| 2004/0176665 A1 | 9/2004 | Branch et al. |
| 2004/0215190 A1 | 10/2004 | Nguyen et al. |
| 2005/0021031 A1 | 1/2005 | Foley et al. |
| 2005/0038432 A1 | 2/2005 | Shaolian et al. |
| 2005/0065517 A1 | 3/2005 | Chin |
| 2005/0070917 A1 | 3/2005 | Justis |
| 2005/0080418 A1 | 4/2005 | Simonson et al. |
| 2005/0085813 A1 | 4/2005 | Spitler et al. |
| 2005/0090822 A1 | 4/2005 | DiPoto |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0154389 A1 | 7/2005 | Selover et al. |
| 2005/0171540 A1 | 8/2005 | Lim et al. |
| 2005/0192485 A1 | 9/2005 | Branch et al. |
| 2005/0192570 A1 | 9/2005 | Jackson |
| 2005/0192589 A1 | 9/2005 | Raymond et al. |
| 2005/0209694 A1 | 9/2005 | Loeb |
| 2005/0245928 A1 | 11/2005 | Colleran et al. |
| 2005/0277934 A1 | 12/2005 | Vardiman |
| 2006/0004455 A1 | 1/2006 | Leonard et al. |
| 2006/0069391 A1 | 3/2006 | Jackson |
| 2006/0074418 A1 | 4/2006 | Jackson |
| 2006/0074445 A1* | 4/2006 | Gerber et al. ............ 606/191 |
| 2006/0079894 A1 | 4/2006 | Colleran et al. |
| 2006/0079909 A1 | 4/2006 | Runco et al. |
| 2006/0084993 A1 | 4/2006 | Landry et al. |
| 2006/0095035 A1 | 5/2006 | Jones et al. |
| 2006/0106380 A1 | 5/2006 | Colleran et al. |
| 2006/0111712 A1 | 5/2006 | Jackson |
| 2006/0111713 A1 | 5/2006 | Jackson |
| 2006/0111714 A1 | 5/2006 | Foley |
| 2006/0111715 A1 | 5/2006 | Jackson |
| 2006/0122602 A1 | 6/2006 | Konieczynski et al. |
| 2006/0149238 A1 | 7/2006 | Sherman et al. |
| 2006/0264962 A1 | 11/2006 | Chin et al. |
| 2006/0293693 A1 | 12/2006 | Farr et al. |
| 2007/0106123 A1 | 5/2007 | Gorek et al. |
| 2007/0191836 A1* | 8/2007 | Justis ............ 606/61 |
| 2007/0191840 A1 | 8/2007 | Pond, Jr. et al. |
| 2007/0233079 A1 | 10/2007 | Fallin et al. |
| 2008/0015582 A1 | 1/2008 | DiPoto et al. |
| 2008/0082103 A1 | 4/2008 | Hutton et al. |
| 2008/0114403 A1 | 5/2008 | Kuester et al. |
| 2008/0140120 A1 | 6/2008 | Hestad et al. |
| 2008/0262318 A1 | 10/2008 | Gorek et al. |
| 2008/0275456 A1 | 11/2008 | Vonwiller et al. |
| 2008/0288005 A1 | 11/2008 | Jackson |
| 2009/0082811 A1 | 3/2009 | Stad et al. |
| 2009/0216328 A1 | 8/2009 | Birkmeyer et al. |

FOREIGN PATENT DOCUMENTS

| | | |
|---|---|---|
| WO | WO-2006091863 | 8/2006 |
| WO | WO-2006116544 | 11/2006 |
| WO | WO-2007035326 | 3/2007 |
| WO | WO-2007087469 | 8/2007 |
| WO | WO-2008024937 | 2/2008 |
| WO | WO-2008039460 A2 | 4/2008 |
| WO | WO-2008130548 A1 | 10/2008 |

OTHER PUBLICATIONS

PCT International Search Report and the Written Opinion mailed Aug. 21, 2008 for PCT/US2008/004856.

* cited by examiner

FIG. 2A1

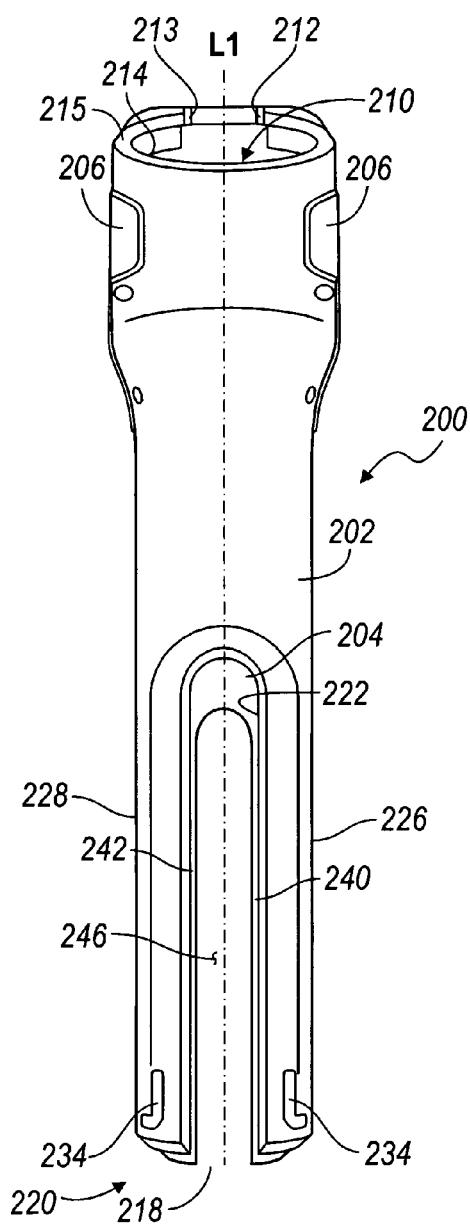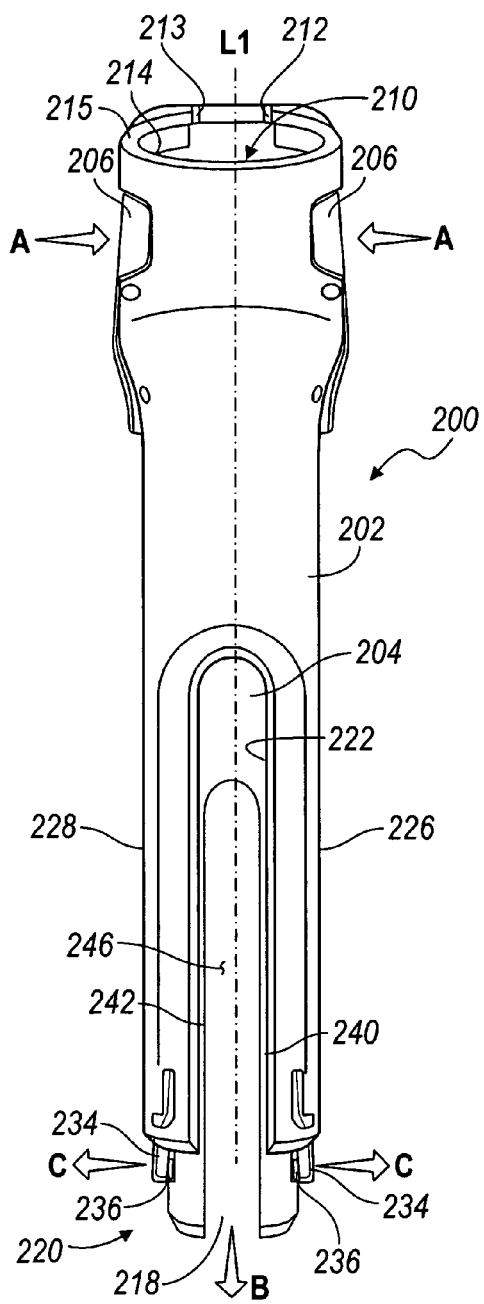
FIG. 2C1      FIG. 2D1

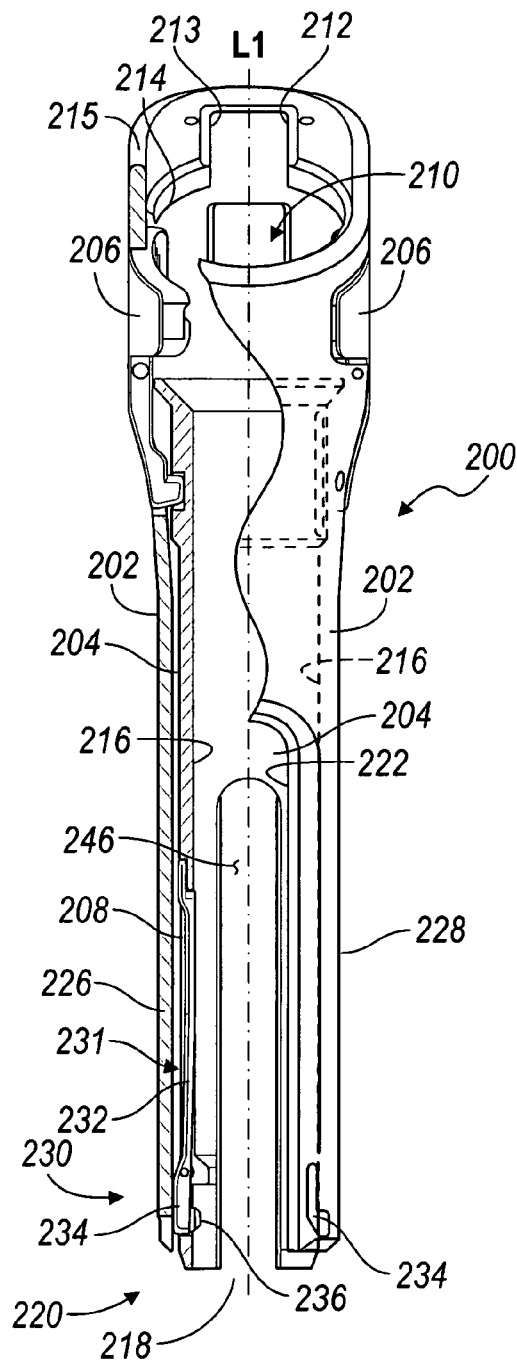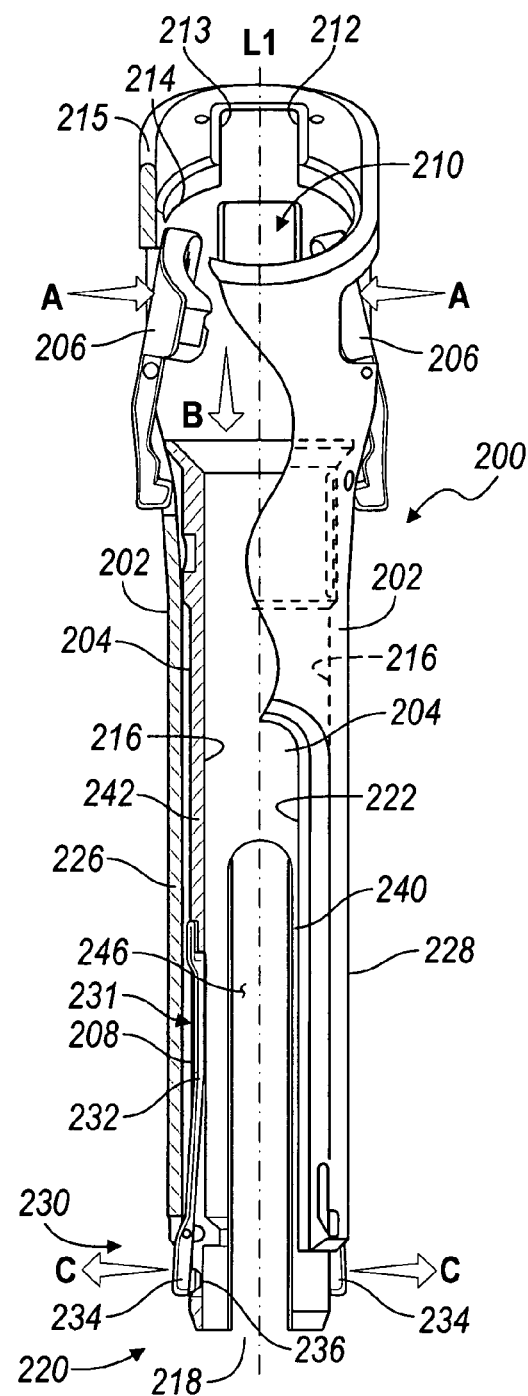
FIG. 2C2     FIG. 2D2

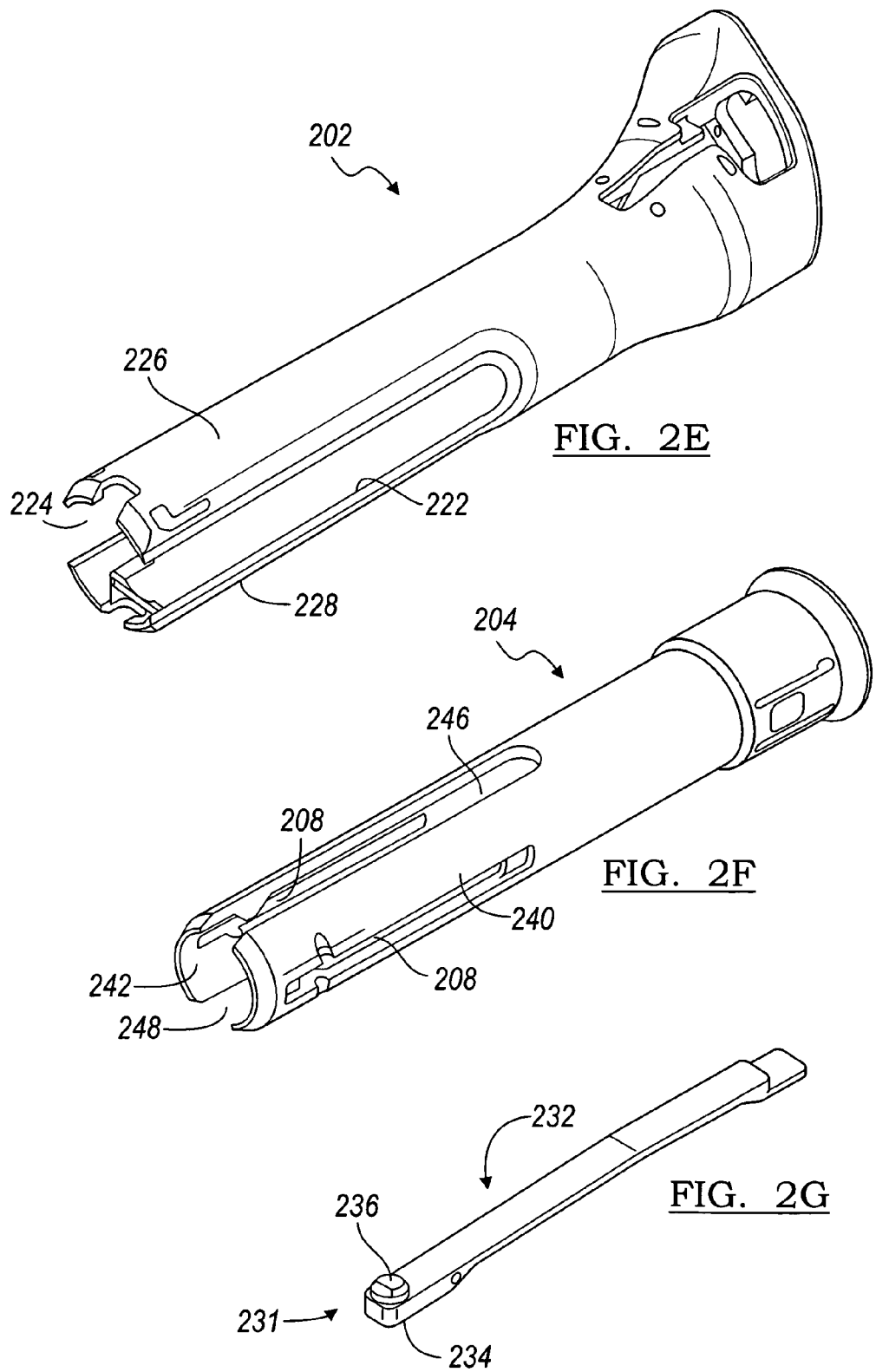

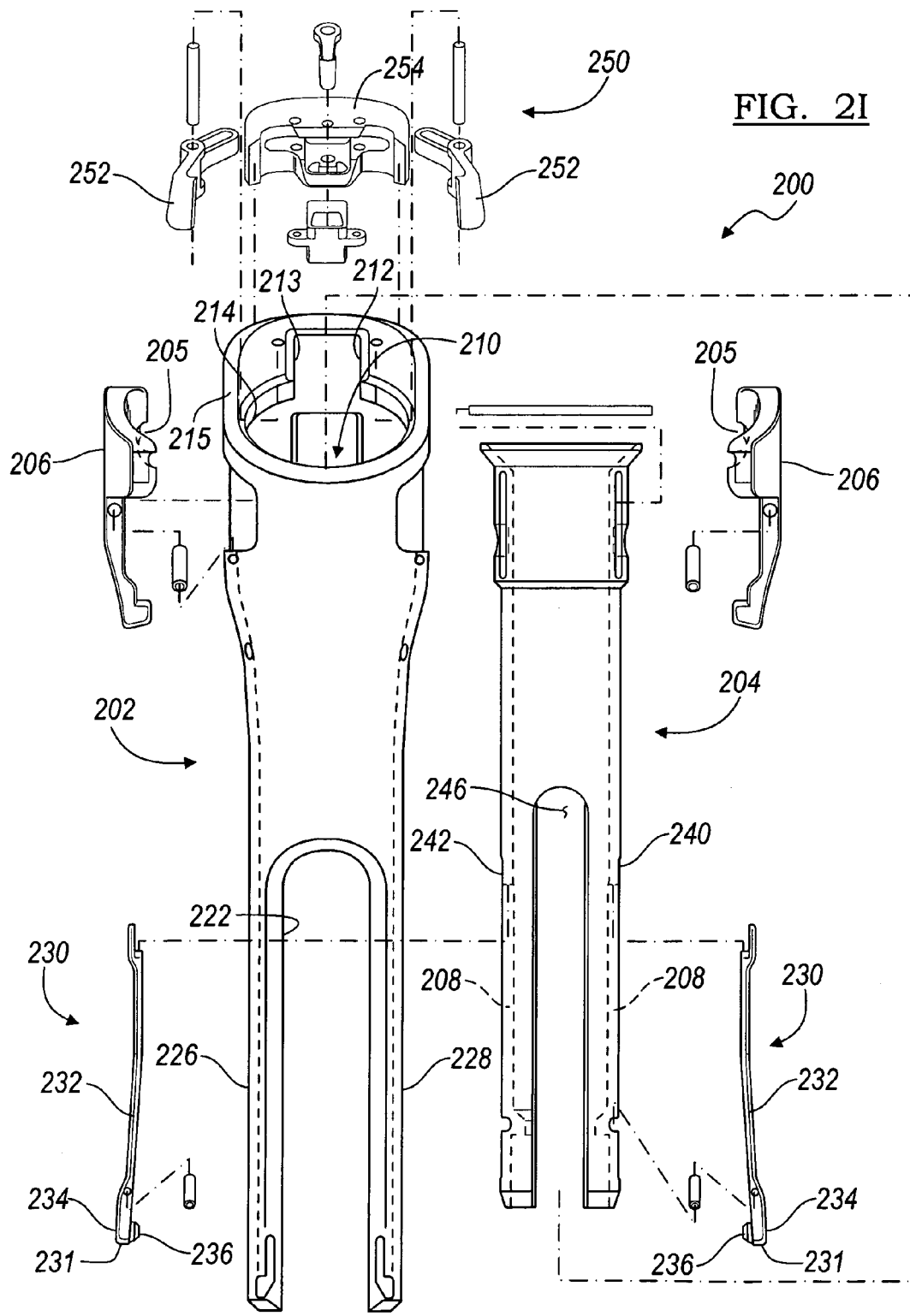

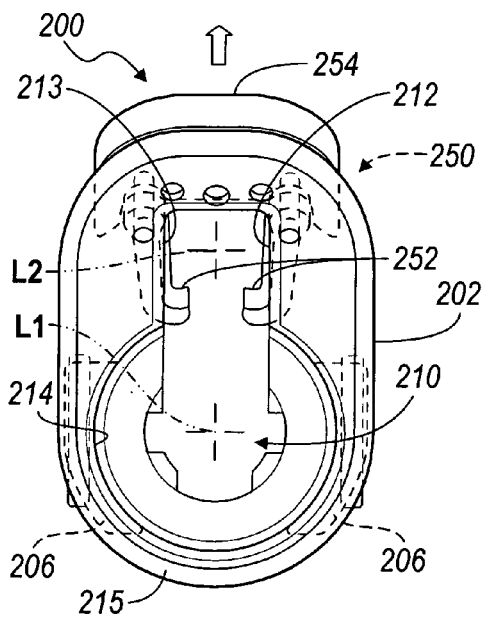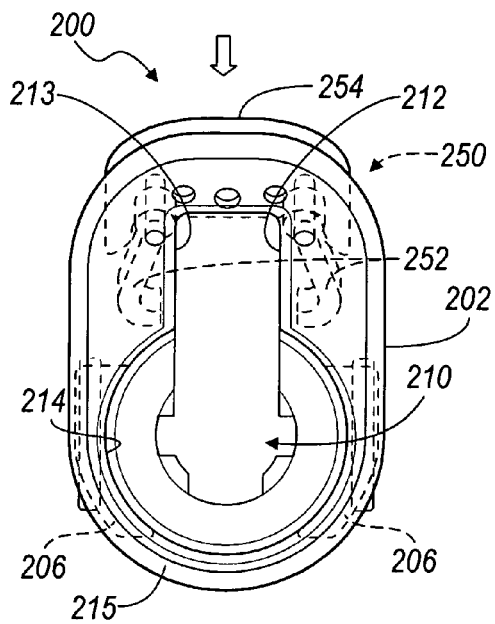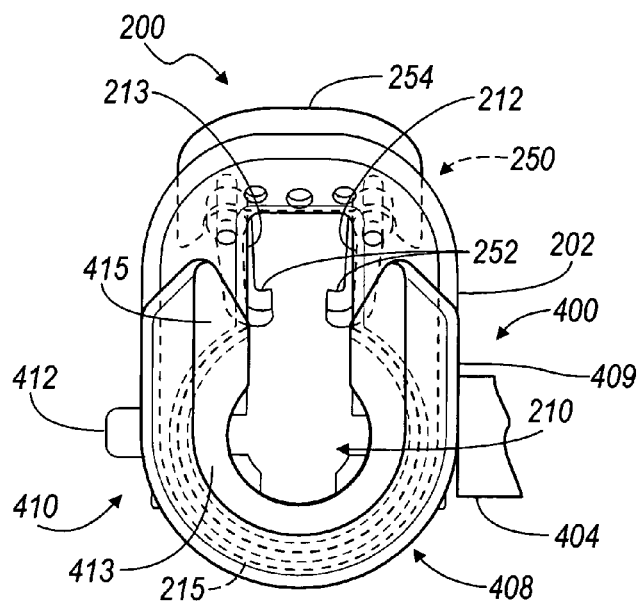

PERCUTANEOUS INSTRUMENT ASSEMBLY

Various stabilization devices and associated methods are known for securing various bones, such as vertebrae of the spine, relative to one another. Such devices include, for example, pedicle screws or other fasteners attached to the vertebrae, connecting elements passing through receivers formed on the pedicle screws, and various instruments for inserting the pedicle screws and mounting the connecting elements on the receivers.

Continuing concern with reducing trauma, infection risk, and patient recovery time, encourages the development of instruments that may help reduce the invasiveness of the procedure. The present teachings provide such a percutaneous instrument assembly and associated methods for spinal procedures.

SUMMARY

The present teachings provide a percutaneous tower for the orthopedic procedures. The tower can include an outer elongated member, an inner elongated member received within the outer elongated member, means for moving the inner elongated member relative to the outer elongated member between first and second positions, and means for engaging a bone fastener when the inner elongated member is in the first position.

In another aspect according to the present teachings, a percutaneous tower for the orthopedic procedures can include an outer elongated member, an inner elongated member received within the outer elongated member, a release actuator operable to move the inner elongated member relative to the outer elongated member between first and second positions, and a fastener engagement member coupled to a distal portion of the tower and operable to engage a bone fastener when the inner elongated member is in the first position, and to disengage the bone fastener when the inner elongated member is in the second position.

In another aspect according to the present teachings, a percutaneous tower for the orthopedic procedures can include an outer elongated member, an inner elongated member received within the outer elongated member, and a release actuator operable to move the inner elongated member relative to the outer elongated member between first and second positions, the inner elongated member at least partially retracted relative to the outer elongated member in first position, the inner elongated member at least partially extended relative to the outer elongated member in the second position, the release actuator communicating with a proximal portion of a first channel of the tower, and a locking element couplable to the tower and operable to lock the release the release actuator in the first position.

In a further aspect according to the present teachings, a percutaneous tower for the orthopedic procedures can include an outer elongated member, an inner elongated member received within the outer elongated member, a pair of release members operable to move the inner elongated member relative to the outer elongated member between first and second positions, and a pair of opposing elements coupled to a distal portion of the inner elongated member, the elements biased to protrude away from the inner elongated member when the inner elongated member is in the second position, each element including a protrusion directed into the tower when the inner elongated member is in the first position.

The present teachings also provide a method for percutaneously implanting a spinal connecting element. The method can include implanting a first bone fastener through a first portal into a first vertebral body, and implanting a second fastener through a second portal into a second vertebral body. The method can further include inserting a connecting element through the first portal in a first orientation substantially perpendicular to the first vertebral body, rotating the connecting element relative to the first orientation such that the connecting element is positioned between the first and second bone fasteners in a second orientation at an angle to the first orientation, and securing the connecting element between the first and a second bone fasteners in the second orientation.

In another aspect, the present teachings provide a method for percutaneously implanting a spinal connecting element. The method can include attaching a first bone fastener to a distal portion of a first channel of a first tower, the first channel defining a first longitudinal axis, the first longitudinal axis passing longitudinally through the first bone fastener, and implanting the first bone fastener into a first vertebral body. The method can further include attaching a second bone fastener to a first channel of a distal portion of a second tower, implanting the second bone fastener into a second vertebral body, inserting the connecting element through a second channel of the first tower, the second channel of the first tower defining a second longitudinal axis substantially parallel to the first longitudinal axis of the first tower and offset in a transverse direction relative to the first longitudinal axis of the first tower, and selectively manipulating the connecting element along a variable-angle path from a position substantially aligned with the second longitudinal axis of the first tower to a position between the first and second bone fasteners.

The present teachings further provide a method of manipulating a first vertebral body relative to a second vertebral body. The method can include engaging a first vertebral body with a first bone fastener connected to a first tower, engaging a second vertebral body with a second bone fastener connected to a second tower, coupling proximal ends of the first and second towers with a compression/distraction mechanism, locking with the compression/distraction mechanism the first and second bone fasteners against accidental release from the first and second towers, operating the compression/distraction mechanism, and moving the first and second towers relative to one another.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2A1 is a perspective view of the locking element of FIG. 2A;

FIG. 2C1 is a perspective view of the percutaneous tower of FIG. 2A shown in a retracted position;

FIG. 2D1 is a perspective view of the percutaneous tower of FIG. 2A shown in a extended position;

FIG. 2C2 is a partially cut-out view of the percutaneous tower of FIG. 2C1;

FIG. 2D2 is a partially cut-out view of the percutaneous tower of FIG. 2D1;

FIG. 2E is a perspective view of an exemplary outer elongated member of the percutaneous tower of FIG. 2A;

FIG. 2F is a perspective view of an exemplary inner elongated member of the percutaneous tower of FIG. 2A;

FIG. 2G is a perspective view of an exemplary flexible or pivotable bar of the percutaneous tower of FIG. 2A;

FIG. 2I is an exploded view of the percutaneous tower of FIG. 2A;

FIG. 3A is a top view of the percutaneous tower of FIG. 2A, shown with a channel divider in a closed position;

FIG. 3B is a top view of the percutaneous tower of FIG. 2A, shown with a channel divider in an open position;

FIG. 3C is a top view of the percutaneous tower of FIG. 2A shown with a tower connector of a compression/distraction mechanism according to the present teachings;

DESCRIPTION OF VARIOUS ASPECTS

The following description is merely exemplary in nature and is in no way intended to limit the invention, its application, or uses. For example, although the present teachings are illustrated for minimally invasive procedures in spinal fusion, or static or dynamic stabilization, the present teachings can be used for other orthopedic surgical applications in which various implants and instruments are manipulated and aligned through a limited area.

Figure 1:
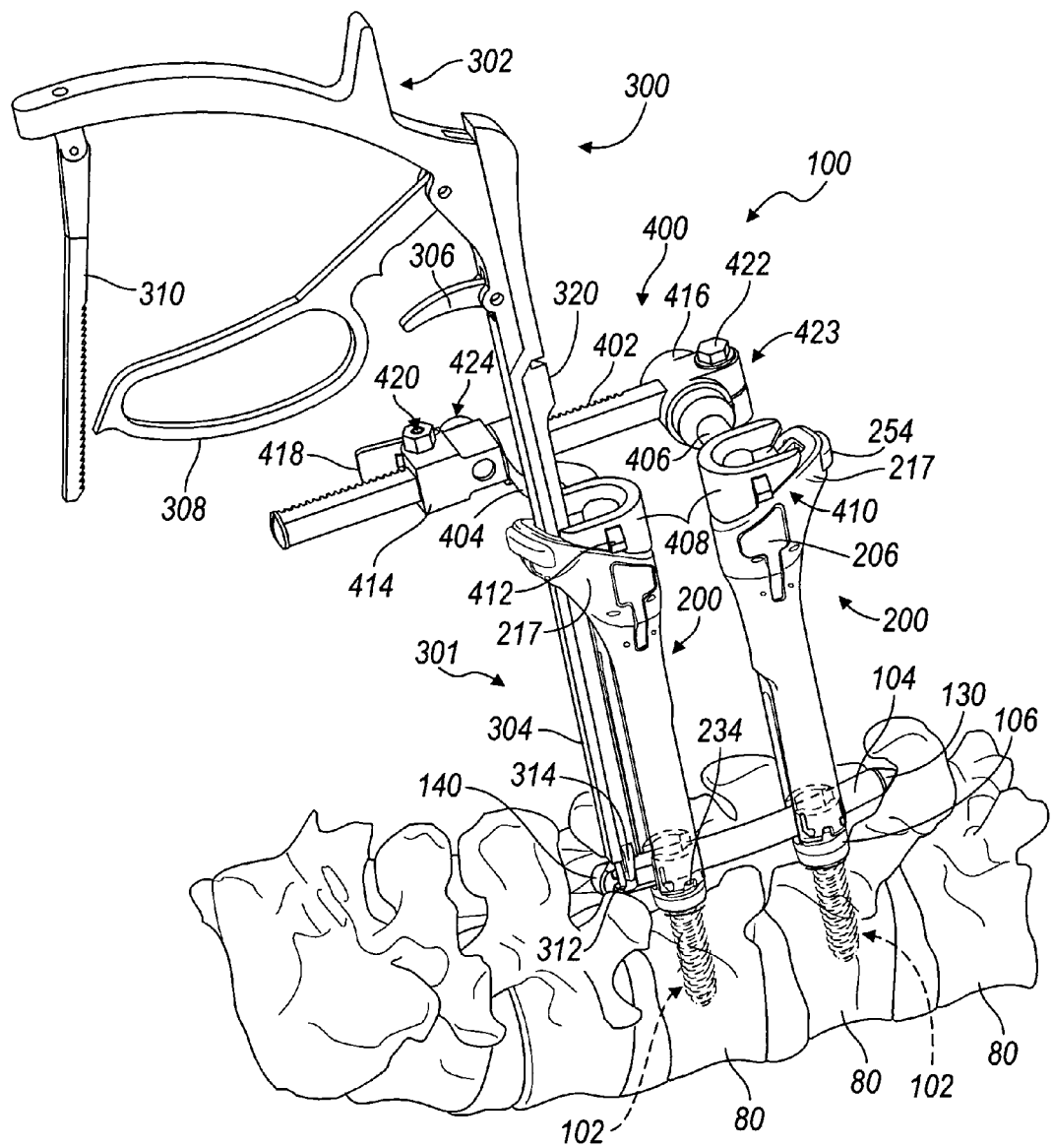
FIG. 1 is a perspective view of an exemplary percutaneous instrument assembly according to the present teachings shown in reference with two adjacent vertebrae.

Referring to FIG. 1, an exemplary percutaneous instrument assembly 100 according to the present teachings can generally include one or more percutaneous towers 200, a percutaneous rod or connecting element inserter 300, and a compression/distraction mechanism 400. It will be appreciated that various other instruments, such as tissue separators, drills, distractors, cannulas, guide wires, bone or pedicle screw inserters, or other instruments can be used in association with the percutaneous instrument assembly 100 at the discretion of the operating surgeon.

As illustrated in FIG. 1, the percutaneous instrument assembly 100 can be used as a spine hardware delivery system that can provide a minimally invasive approach for spine fusion procedures, static or dynamic spine stabilization, or other orthopedic procedures. The percutaneous towers 200 of the percutaneous instrument assembly 100 can be used to implant or remove bone or pedicle screws, bone anchors, or other bone fasteners 102 into the vertebral bodies 80 of the spine. The percutaneous towers 200 can also be used to advance a percutaneous connecting element 104, such as a connecting rod or bar or other elongated element, using the percutaneous rod inserter 300.

As a preparatory matter, utilizing anterior/posterior and lateral fluoroscopic imaging and palpation of the patient's appropriate vertebral landmarks, the targeted pedicles can be located and marked on the patient's skin. A percutaneous skin incision and fascia release in the form of a small portal can be made with a knife blade, a Jamshidi-type needle, or other cutting instrument at the location marks on the patient's skin and a needle or similar instrument can be advanced through the skin incision. The needle can be docked onto the targeted pedicle and verified with fluoroscopic imaging. Once trajectory and docking of the needle is confirmed and complete, the needle can be removed and replaced by guide wire.

Dilation of the opening of the incision through the muscles can be performed, for example, in a two-staged sequential manner over the guide wire. A cannulated tap can be advanced over the guide wire and the pedicle can be prepared for the implantation of a cannulated bone anchor, such as the bone fastener 102. The bone fastener 102 can then be assembled onto the distal end of the percutaneous tower 200.

Figure 2A:
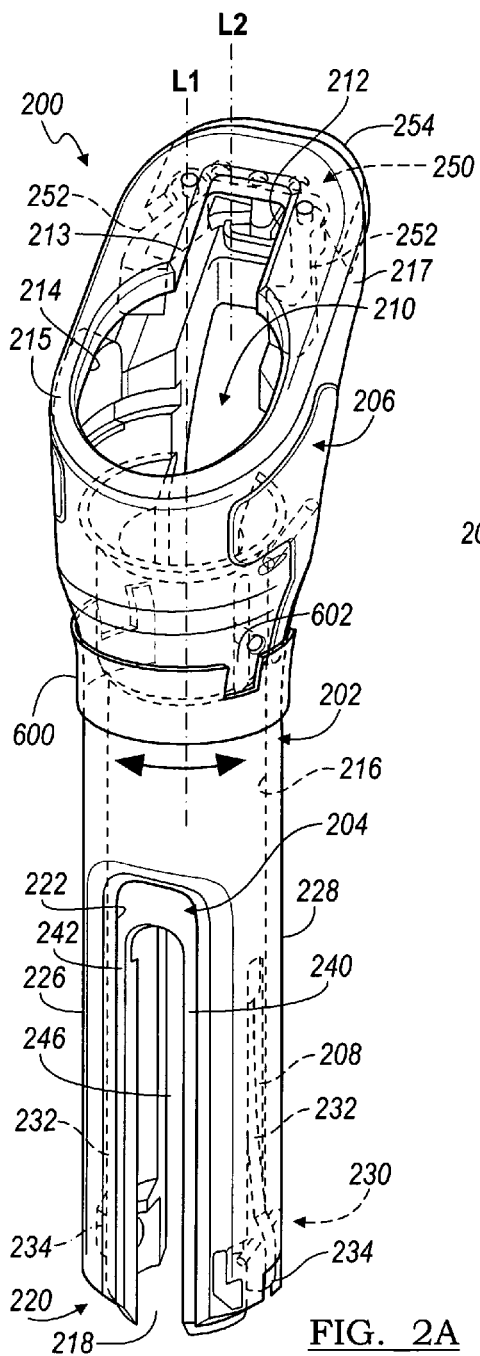
FIG. 2A is a perspective view of an exemplary percutaneous tower according to the present teachings, shown with a locking element.
Figure 2B:
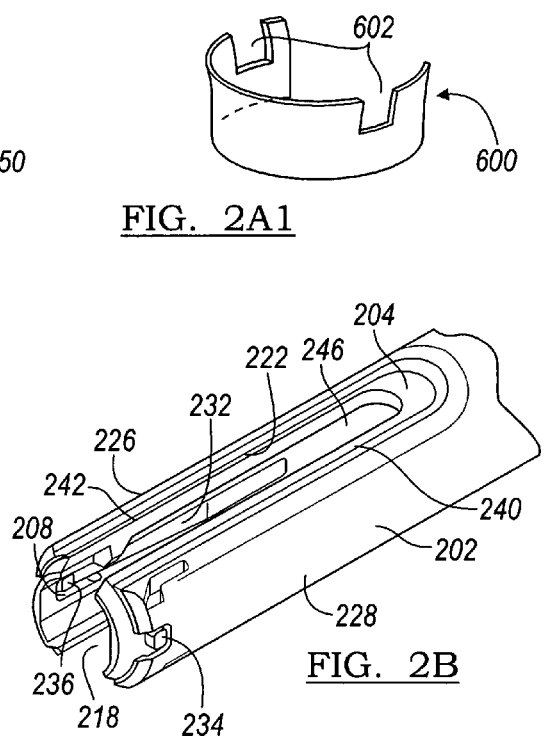
FIG. 2B is a perspective view of a distal portion of the percutaneous tower of FIG. 2A.

Referring to FIGS. 2A-3B, each percutaneous tower 200 can include an outer elongated member or outer shaft 202 and an inner elongated member or inner shaft 204. The outer and inner elongated members 202, 204 can be coupled for allowing limited sliding relative to one another providing quick connection or disconnection for a fastener engagement member 230 that can be used to secure the bone fastener 102 to the percutaneous tower 200 without requiring additional locks or manipulating steps. Referring to FIGS. 2D1 and 2D2, quick disconnection can be effected through manual depression of a release actuator feature of the tower 200 in the direction of arrows "A". In this regard, one or more release buttons 206 can be simultaneously depressed, thereby allowing the bone fastener 102 to be released, as described below. The release buttons 206 are pivotably coupled to the proximal portions of the outer elongated member 202, such that the inner elongated member 204 can move relative to the outer elongated member 202 from a first "retracted" position shown in FIGS. 2C1 and 2C2 in which the fastener engagement member 230 is in an engagement configuration relative to the bone fastener 102, to a second "extended" position, shown in FIGS. 2D1 and 2D2 downwardly translated in the direction of arrow "B", in which the fastener engagement member 230 is in a disengagement configuration relative to the bone fastener 102.

Referring to FIGS. 2A and 2A1, the percutaneous tower can include a locking element 600 for locking the release buttons 206 and preventing their accidental depression. The locking element 600 can be in the form of a split ring or other U-shaped element. The locking element 600 can be fitted over the outer elongated member 202 as shown in FIG. 2A. The locking element 600 can include two pockets, cutouts or other openings 602. The openings 602 can be configured to allow pivoting of the release buttons 206 in the unlocked position. For example, the distal ends of the release buttons 206 can swing outward relative to the tower 200 through the openings 602 of the locking element 600 in the unlocked position of the locking element 600. The locking element 600 can be rotated from the unlocked position to a locked position in which the release buttons 206 can be prevented from pivoting, such that the distal ends of the release buttons 206 can be prevented from swinging out relatively to the tower 200.

Referring to FIGS. 2A-D2, 2G and 2H, the fastener engagement member 230 can include two elements in the form of one or more flexible (elastically deflectable) or pivotable bars 232 that can engage respective opposing slots 208 of the inner elongated member 204. The bars 232 can be held between the outer and inner elongated members 202, 204 against outward bias. Each bar 232 can include a tab 234 and a protrusion 236 at opposite ends of its distal end 231. When the inner elongated member 204 is in the retracted position shown in FIGS. 2B, 2C1 and 2C2, the tabs 234 are held inwards by the outer elongated member 202, such that the protrusions 236 extend transversely into a first longitudinal opening, hole or channel 210, which extends along a first longitudinal axis L1 of the tower 200. As shown through the drawings, the longitudinal axis L1 of the tower 200 can pass through the proximal portion of the associated bone fastener 102.

In the retracted position of the inner elongated member 204, the protrusions 236 can engage corresponding engagement slots 108 in a receiver portion 106 of the bone fastener 102, shown in FIG. 2H, as described below. When the inner elongated member 204 is in the extended position shown in FIGS. 2D1 and 2D2, the tabs 234 move outwards in the direction of arrows "C" protruding out of the slots 208 of the inner elongated member 204 and becoming disengaged from the engagement slots 108 of the receiver portion 106 of the bone fastener 102. It will be appreciated that the bone fastener 102 can be held by either the outer elongated member 202 or the inner elongated member 204 at the distal end of the tower 200.

Each tower 200 can at least partially define or include the first channel 210 discussed above and a second channel 212 which extends along a second axis L2. The first channel 210 can extend from a curved opening 214 at a proximal end 215 of the outer elongated member 202 through a common bore 216 of the outer and inner elongated members 202, 204 to an opening 218 at a distal end 220 of the tower 200. The second channel 212 can communicate with the first channel 210. The second channel 212 can be offset from the first channel 210 in a direction transverse to the first axis L1 such that the axes L1 and L2 are parallel, but not coinciding. The second channel 212 is formed in an angled portion 217 of the proximal end 215 and includes an offset opening 213, which can extend from the curved opening 214 in a U-shape form. It another aspect, the second channel 212 can be angled and such that the second axis L2 coincides with the first axis L1.

Figure 10:
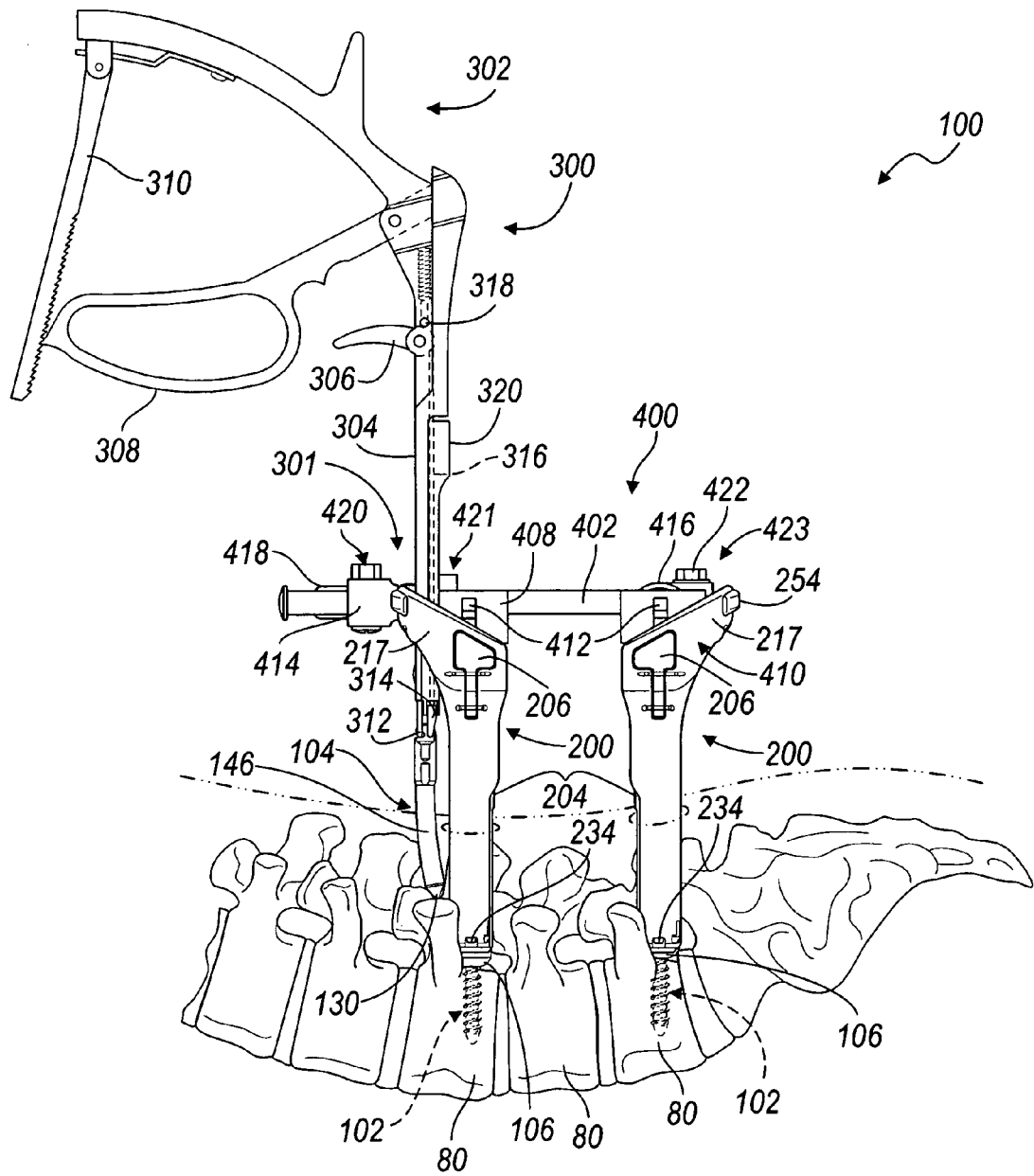
FIG. 10 is a side view of an exemplary percutaneous instrument assembly according to the present teachings illustrating a percutaneous rod inserter guiding a connecting element through a channel of a percutaneous tower connected to a vertebral body.
Figure 11:
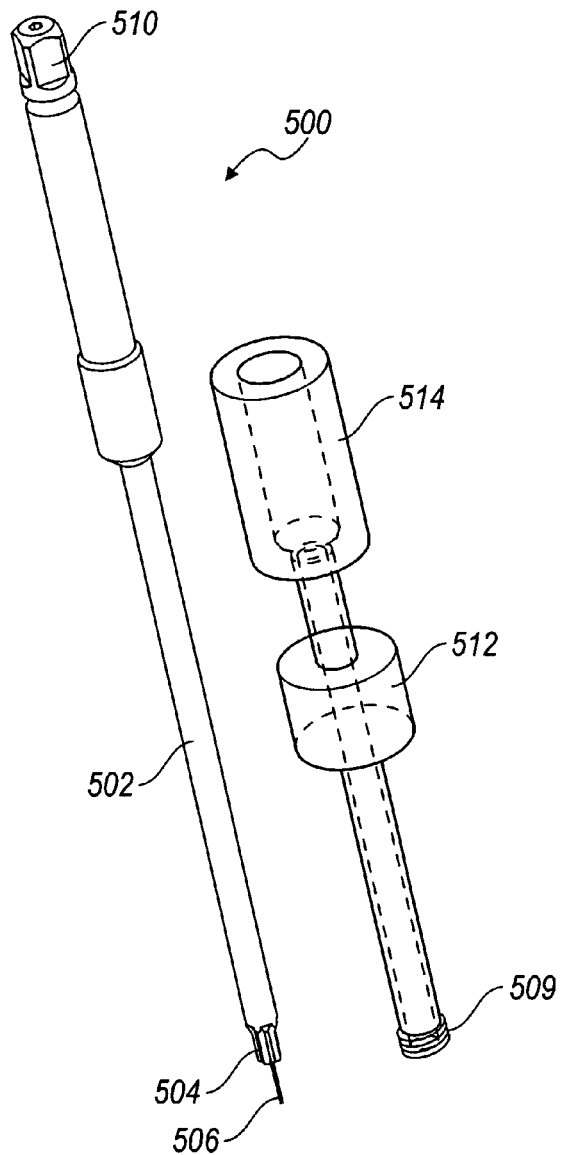
FIG. 11 is an exploded view of an exemplary fastener inserter according to the present teachings.
Figure 11A:
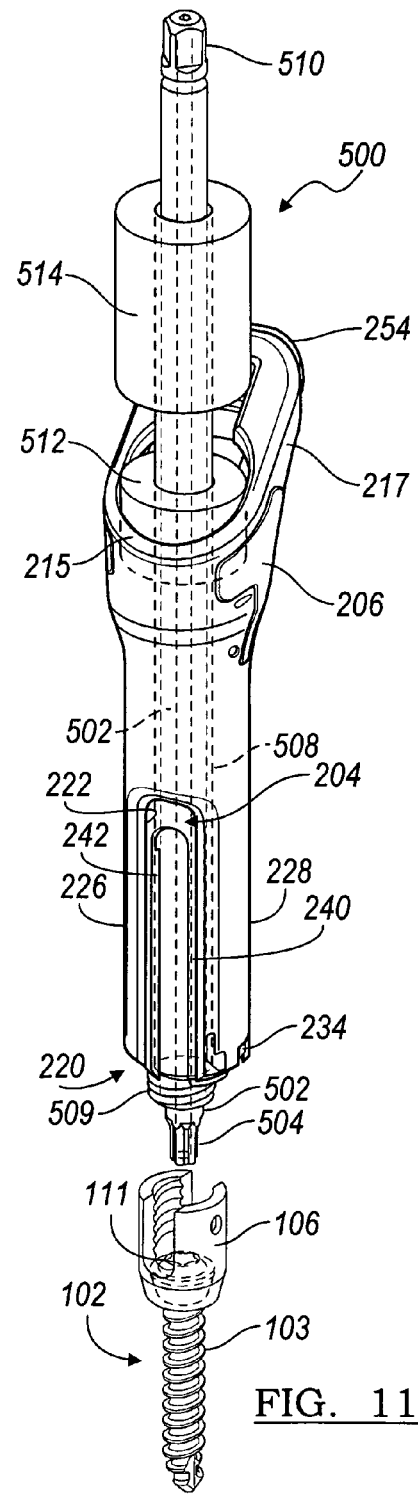
FIG. 11A is perspective view of the fastener inserter of FIG. 11 shown assembled through a percutaneous tower according to the present teachings.

The first and second channels 210, 212 can be used to support or pass various instruments and implants, such as, for example, an elongated distal portion 301 of the percutaneous rod inserter 300, the connecting element 104, as shown in FIGS. 1 and 10, tower connectors 408 of the compression/distraction mechanism 400, a bone fastener inserter 500, as shown in FIG. 11A, and other instruments and implants, as discussed below.

Referring to FIGS. 2A, 2I, and 3A-C, a spring-loaded channel divider 250 can be coupled to the proximal end 215 of the outer elongated member 202. As discussed below, the channel divider 250 can function to selectively and optionally separate the first and second channels 210, 212 The channel divider 250 can include a base 254 slidably coupled to the proximal end 215, and two arms 252 pivotably coupled to the base 254. The base 254 can be moved between first and second positions as shown in FIGS. 3A and B. In the first position, shown in FIG. 3A, the arms 252 are forced closer to each other, such that end portions of the arms 252 extend between the first and second channels 210, 212, keeping the first and second channels 210, 212 separated. In the second position, shown in FIG. 3B, the arms 252 spring outwards away from the openings of the first and second channels 210, 212 to allow instruments and implants to pass freely between the first and second channels 210, 212.

Figure 4A:
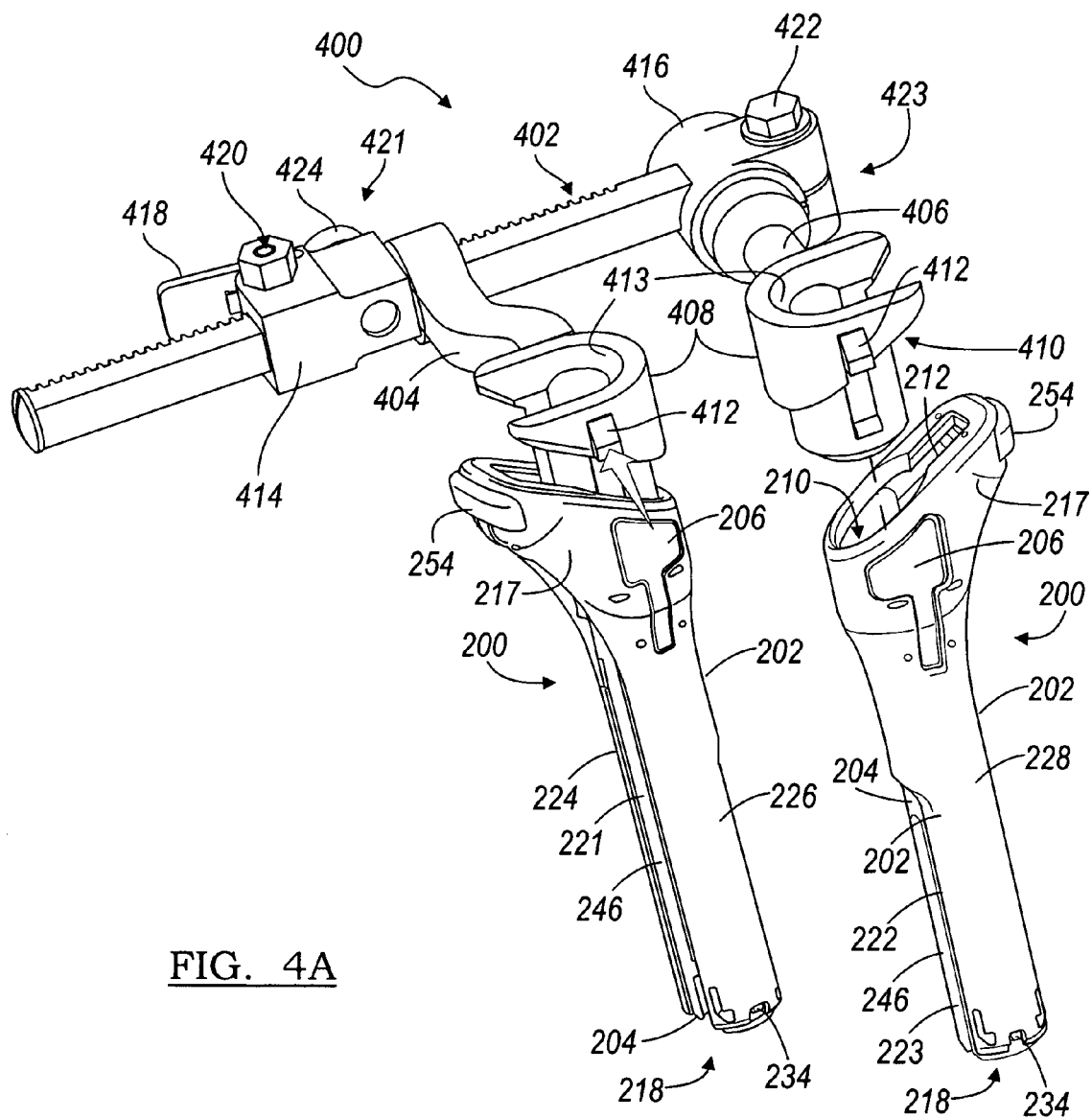
FIG. 4A is a partially exploded perspective view of an exemplary percutaneous instrument assembly according to the present teachings shown with two exemplary percutaneous towers and an exemplary compression-distraction mechanism.
Figure 4B:
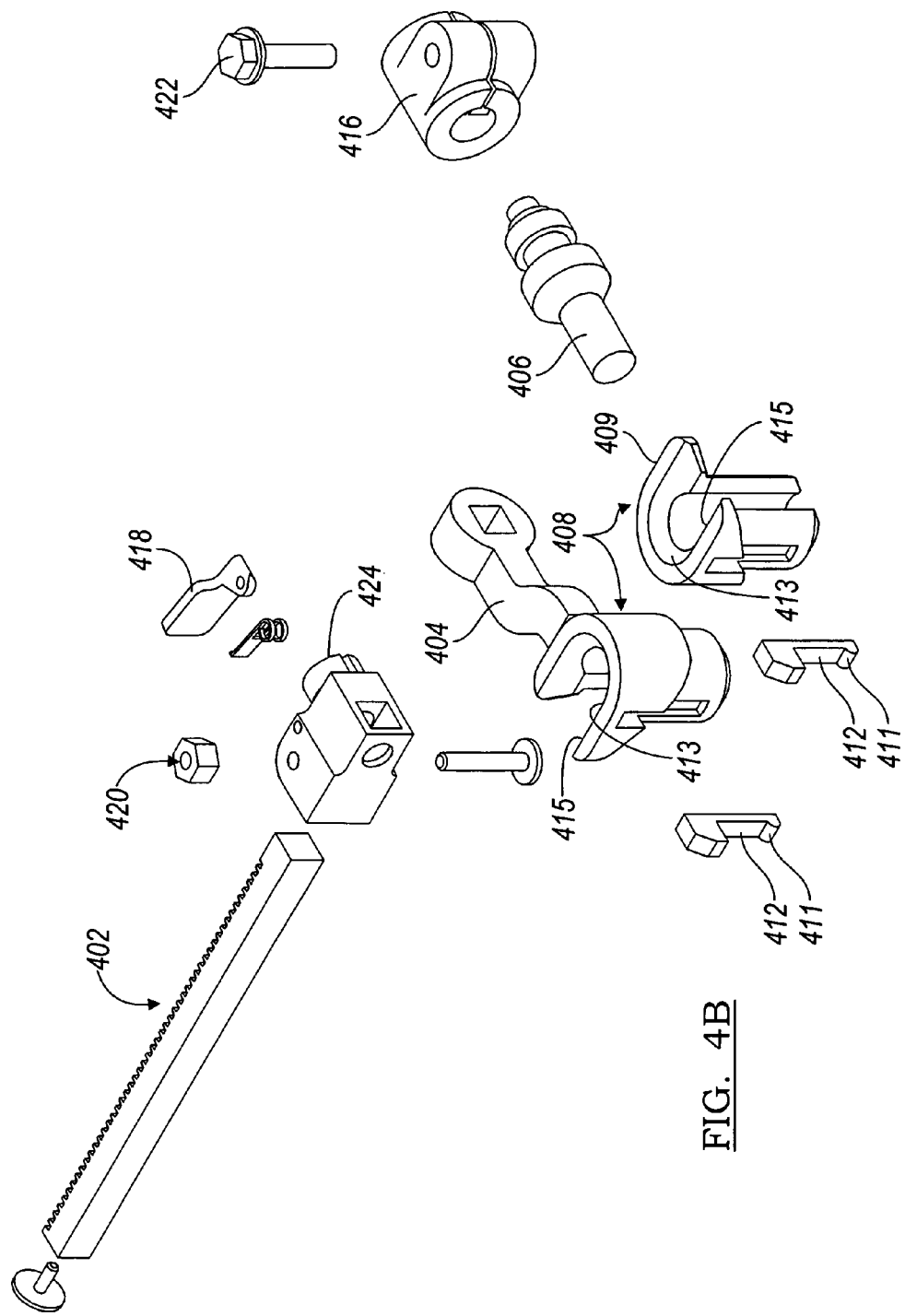
FIG. 4B is an exploded view of an exemplary compression-distraction mechanism according to the present teachings.

Referring FIGS. 2A, 2E, 2F and 4A, each tower 200 can also have first and second longitudinal slots 221, 223 defined by corresponding first and second slots 224, 222 in the outer elongated member 202 and first and second slots 248, 246 in the inner elongated member 204. Referring to FIG. 4A, the first slot 221 can be longer and can be placed on the side of the angled portion 217 of the tower 200 to provide additional space for instrumentation. The second slot 223 can be shorter and can be placed opposite the first slot 221 for guiding the connecting element 104 as it exits or enters one of the towers 200. The first and second slots 224, 222 of the outer elongated member 202 define first and second opposing legs 226, 228 at the distal end of the outer elongated member 202. Similarly, the first and second slots 248, 246 of the inner elongated member 204 define first and second opposing legs 242, 240 at the distal end of the inner elongated member 204.

Referring to FIGS. 4A-5B, an exemplary compression-distraction (C/D) mechanism 400 adapted for use with the towers 200 is illustrated. The C/D mechanism 400 can include a dial-type linear control 421 and a dial-type rotational control 423. The linear control 421 can adjust the distance between the percutaneous towers 200, and the rotational control 423 can adjust the angle of the towers 200 relative to each other and to the patient. The linear control 421 of the C/D mechanism 400 can also determine the distance between the percutaneous towers 200, and therefore it can be used to determine the length of the connecting element 104 that is required for a particular surgical procedure. In this regard, the C/D mechanism 400 can be provided with indicia representative of a distance between the associated bone fasteners 102. When the tower connectors 200 are not aligned in parallel, a mathematical formula based on the geometric relation and the relative angles of the towers 200 can be used to determine the appropriate length of the connecting element 104.

The C/D mechanism 400 can include a rack 402 and first and second arms 404, 406, each of the arms 404, 406 coupled to a tower connector 408. In the exemplary illustration of the C/D mechanism 400, the first arm 404 can slide along the rack 402 in the direction of the straight arrows "T". The second arm 406 can be fixed relative to the rack 402 and can rotate about its axis "A1" such that the tower connector 408 that is attached to the second arm 406 can angulate relative to the rack 402 and relative to the tower connector 408 that is connected to the first arm 404 in the directions shown by the curved arrows "R" in FIG. 5B. Each tower connector 408 can be configured to be received in the proximal portion of the tower 200 and can include first and second channels 413, 415 channels similar to the first and second channels 210, 212 of the tower 200 enabling the instruments and implants to pass freely through both devices.

Each tower connector 408 can include a key feature 409, which is configured to complement the angled portion 217 of the proximal end 215 of the tower 200. The key feature 409 prevents rotation of the tower connector 408 relative to the tower 200 and allows coupling in only one direction. The tower connector 408 can also include a quick-connect, button-style mechanism 412 having a tab 411 that can engage an internal groove 205 of the release button 206 of the tower 200 (shown in FIG. 2I). When the tower connector 408 is attached to the tower 200, the tower connector 408 can act as a safety lock, similarly to the locking element 600, pushing against the inner surfaces of the release buttons 206 and preventing activation of the release buttons 206, thereby preventing accidental release of the bone fastener 102 from the tower 200.

Figure 5A:
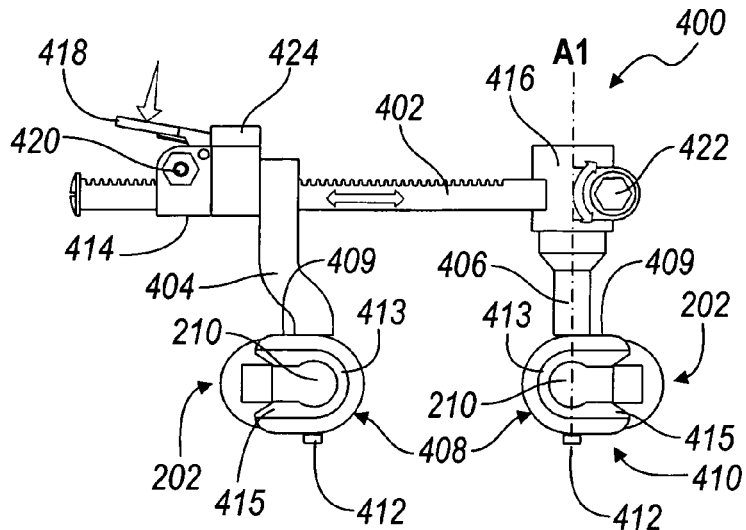
FIG. 5A a top view of an exemplary percutaneous instrument assembly according to the present teachings shown with two exemplary percutaneous towers and an exemplary compression/distraction mechanism.
Figure 5B:
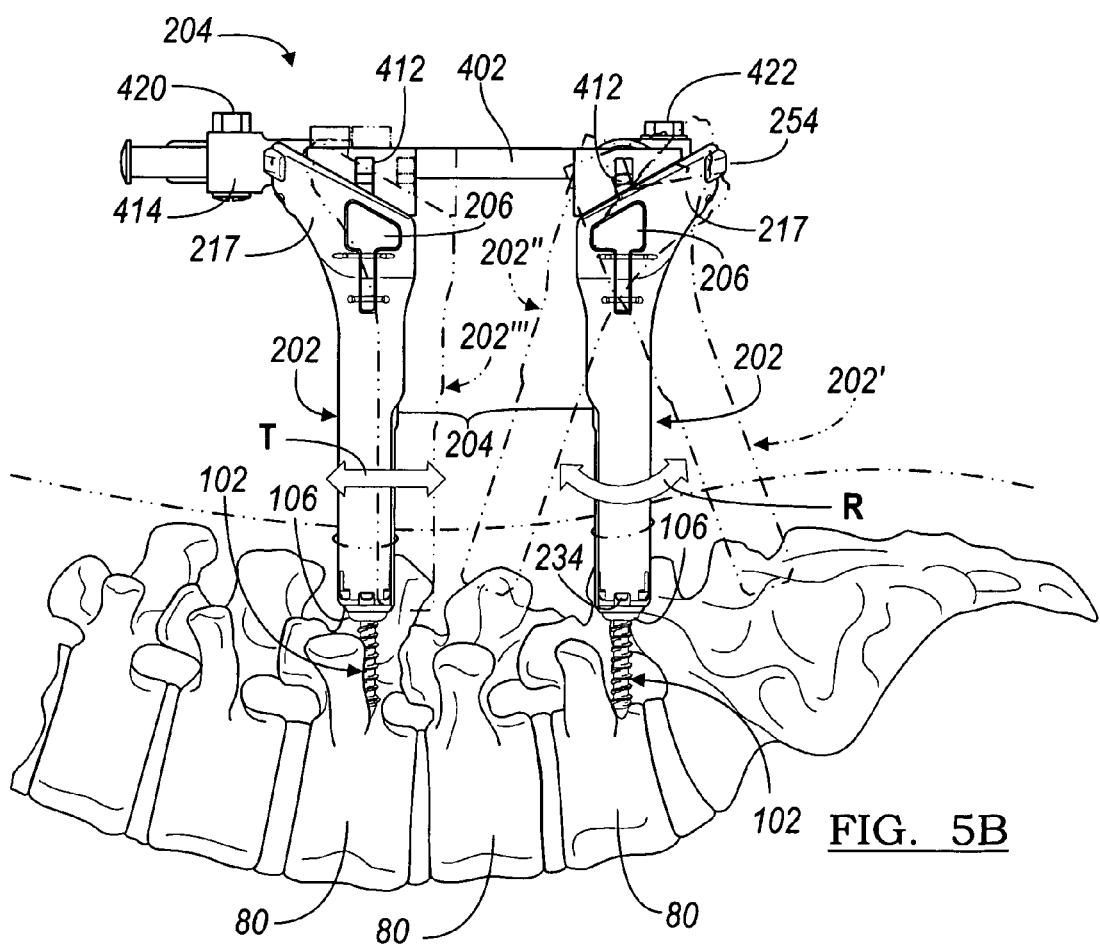
FIG. 5B is a side view of an exemplary percutaneous instrument assembly according to the present teachings illustrating an exemplary compression/distraction mechanism relative to vertebral bodies.
Figure 6A:
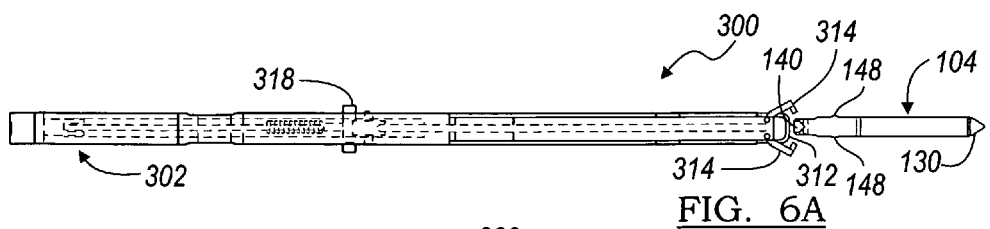
FIG. 6A is a top view of a portion of a percutaneous rod inserter before engaging or after releasing a connecting element according to the present teachings.
Figure 6B:
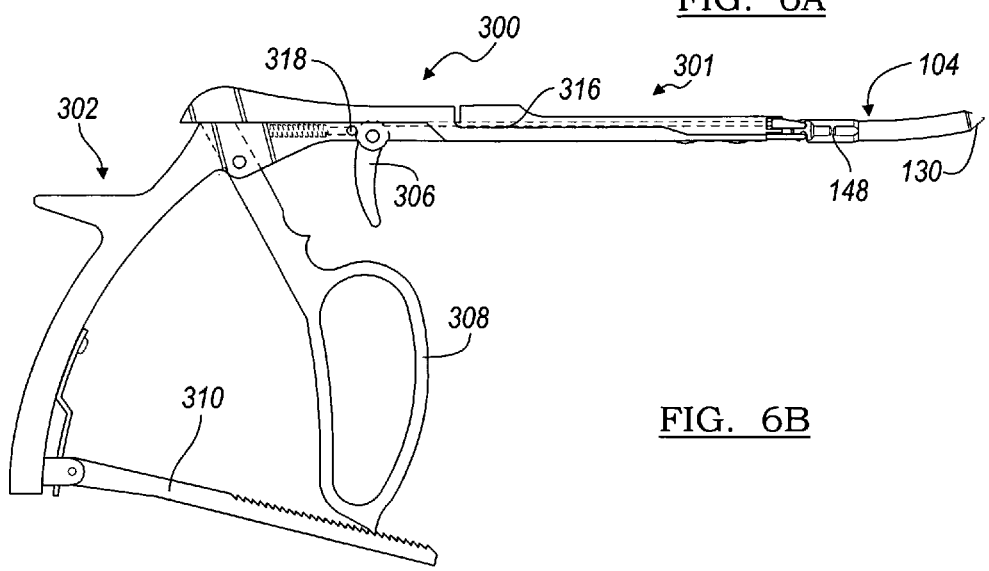
FIG. 6B is a side view of a percutaneous rod inserter shown in engagement with a connecting element according to the present teachings.

Referring to FIGS. 4A, 5A, and 5B, the C/D mechanism 400 can include a directional lock 424, which can be a knob with first and second settings. In the first setting, the first arm 404 can be moved along the rack 402 bringing the first and second arms 404, 406 and the corresponding tower connectors 408 closer to one another for compression. In the second setting, the first arm 404 can be moved along the rack 402 to position the first and second arms 404, 406 and the corresponding tower connectors 408 further apart relative to one another for distraction. When one of the first and second settings of the directional lock 424 is selected, the first arm 404 can slide along the rack 402 in the selected direction by turning a position control knob 420. A lock release control 418 can be provided and operate to incapacitate the directional lock 424, such that the first arm 404 is free to move in either direction for compression or distraction.

Referring to FIGS. 5A and B, the C/D mechanism 400 can include an angulation control 422 which can be rotated to rotate the second arm 406 about its axis A1 causing the respective tower 200 to angulate in the direction of the arrows R towards or away from the tower 200 that is coupled to the first arm 404, as illustrated in FIG. 5B.

Referring to FIGS. 6A-10, the percutaneous rod inserter 300 is illustrated in exemplary positions relative to the connecting element 104. The rod inserter 300 can include a rongeur-type body 302 including a rack bar 310, an angle handle 308 that can be coupled to various positions along the rack bar 310, a release trigger 306, and an elongated distal portion 301 insertable through the first 210 or second channel 212 of the tower 200. The elongated distal portion 301 can include mechanisms for releasably coupling the connecting element 104 to the rod inserter 300, such that the connecting element 104 can be held in a first position in which a longitudinal axis "E" of the connecting element 104 is substantially parallel or coaxial to a longitudinal axis "D" of the elongated distal portion 301 of the rod inserter 300, as shown in FIGS. 8C and 9B, and in a second position in which the connecting element 104 is at an angle α relative to the elongated distal portion 301 of the rod inserter, as shown in FIGS. 8D and 9C.

The angle handle 308 can be operably coupled to an angle arm 304 that can include a U-shaped distal portion 312 adapted to pivotable engage an open slot 142 in the proximal end of the connecting element 104. Pressing the angle handle 308 in the direction of arrow "G2" causes the angle arm 304 to move forward in the direction of arrow "H2" and urges the connecting element 104 to pivot at an angled position relative to the elongated distal portion 301 of the percutaneous rod inserter 300, as shown in FIGS. 9C and 8D. Conversely, pushing the angle handle 308 in the direction of arrow "G1" urges the angle arm 304 to move backward in the direction of arrow "H1" forcing the connecting element 104 to straighten out along the elongated distal portion 301 of the rod inserter 300, as shown in FIGS. 9B and 8C. It will be appreciated that the direction of motion associated with arrows H1, H2 and G1, G2 can be reversed.

Figure 8A:
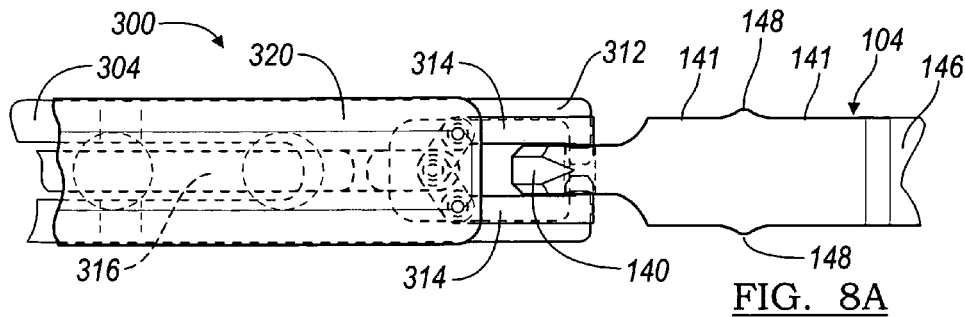
FIG. 8A is plan view of a percutaneous rod inserter shown with locking arms in engagement with a connecting element according to the present teachings.
Figure 8B:
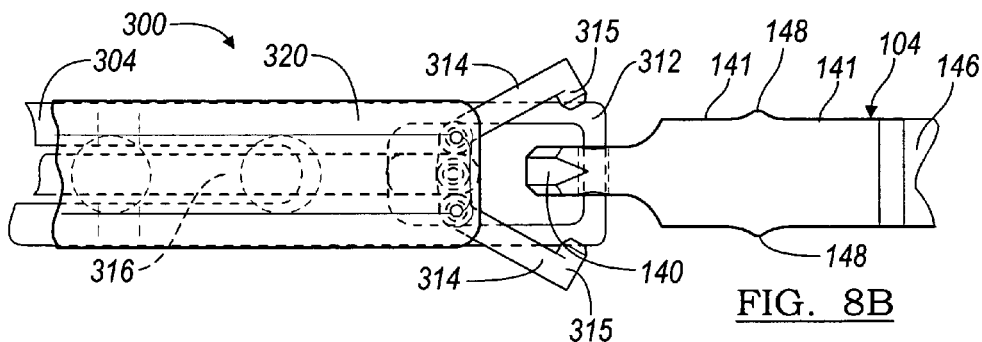
FIG. 8B is a plan view of a percutaneous rod inserter shown with locking arms disengaged from a connecting element according to the present teachings.
Figure 8C:
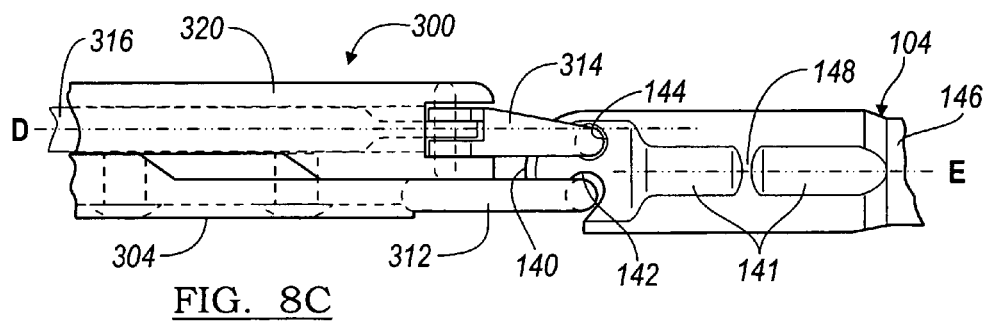
FIG. 8C is a side view of the percutaneous rod inserter and connecting element of FIG. 8A.
Figure 8D:
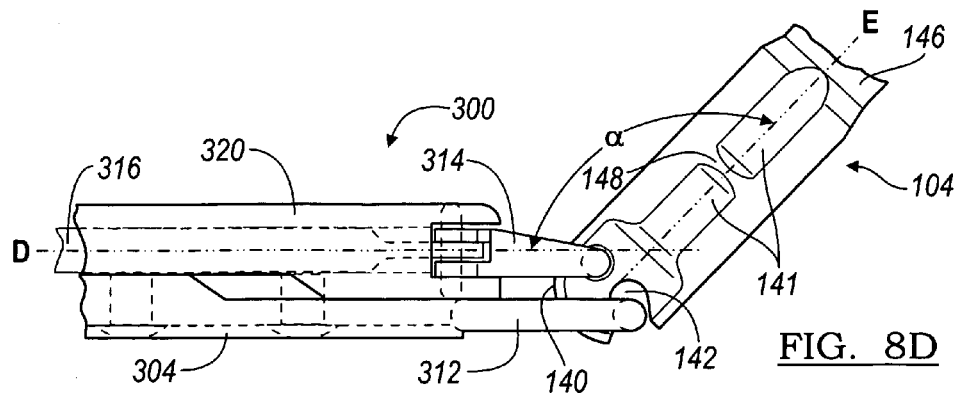
FIG. 8D is a side view of the percutaneous rod inserter and connecting element of FIG. 8A, with the connecting element shown in an angled position.
Figure 9A:
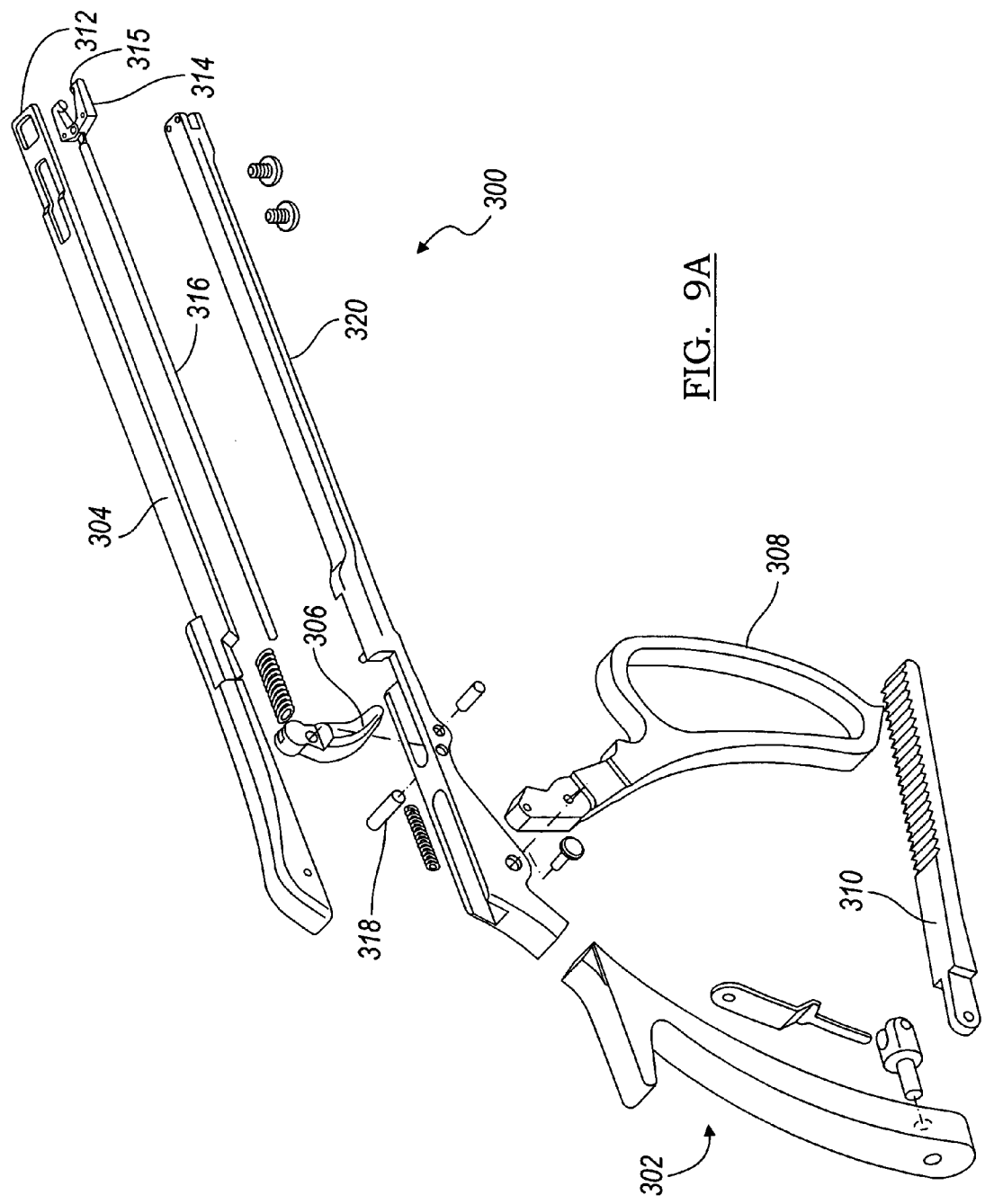
FIG. 9A is an exploded view of an exemplary percutaneous rod inserter according to the present teachings.
Figure 9B:
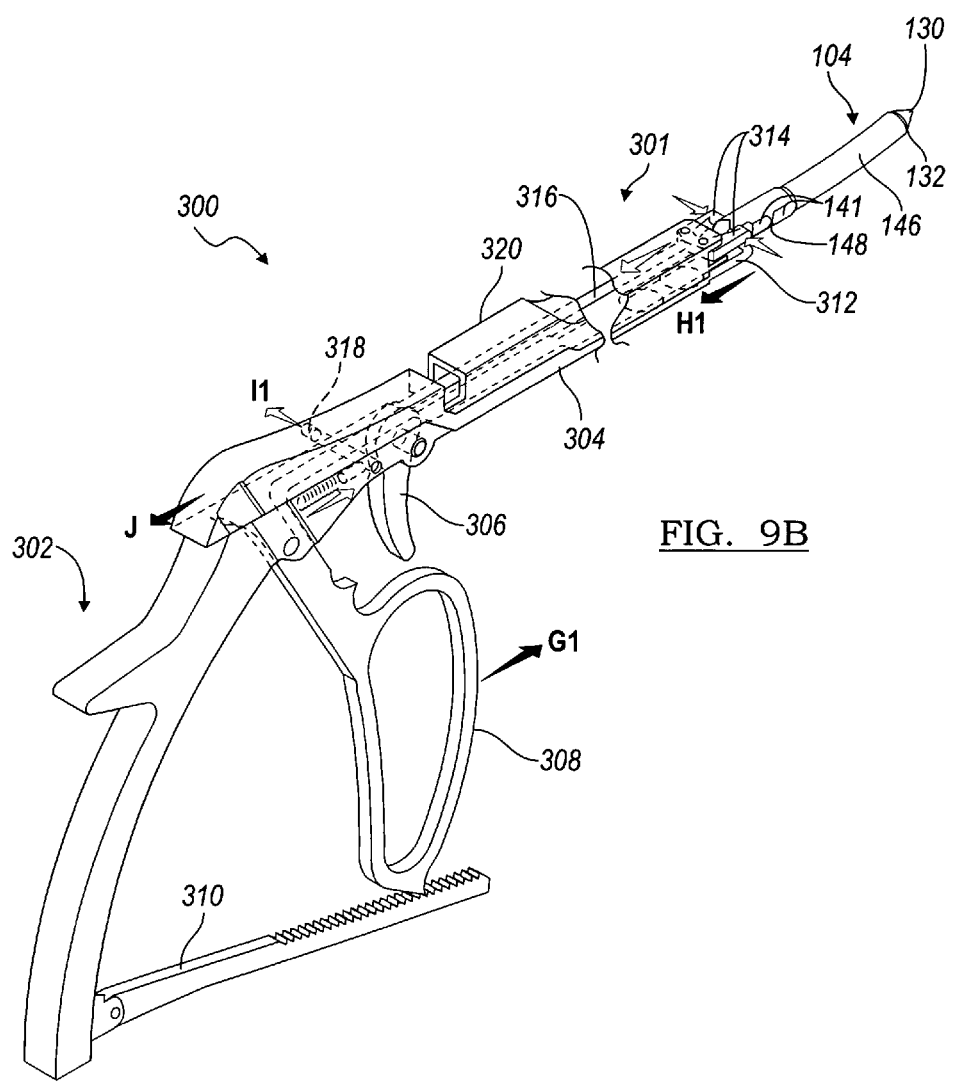
FIG. 9B is a perspective view of the percutaneous rod inserter of FIG. 9A shown with a connecting element in a first position.
Figure 9C:
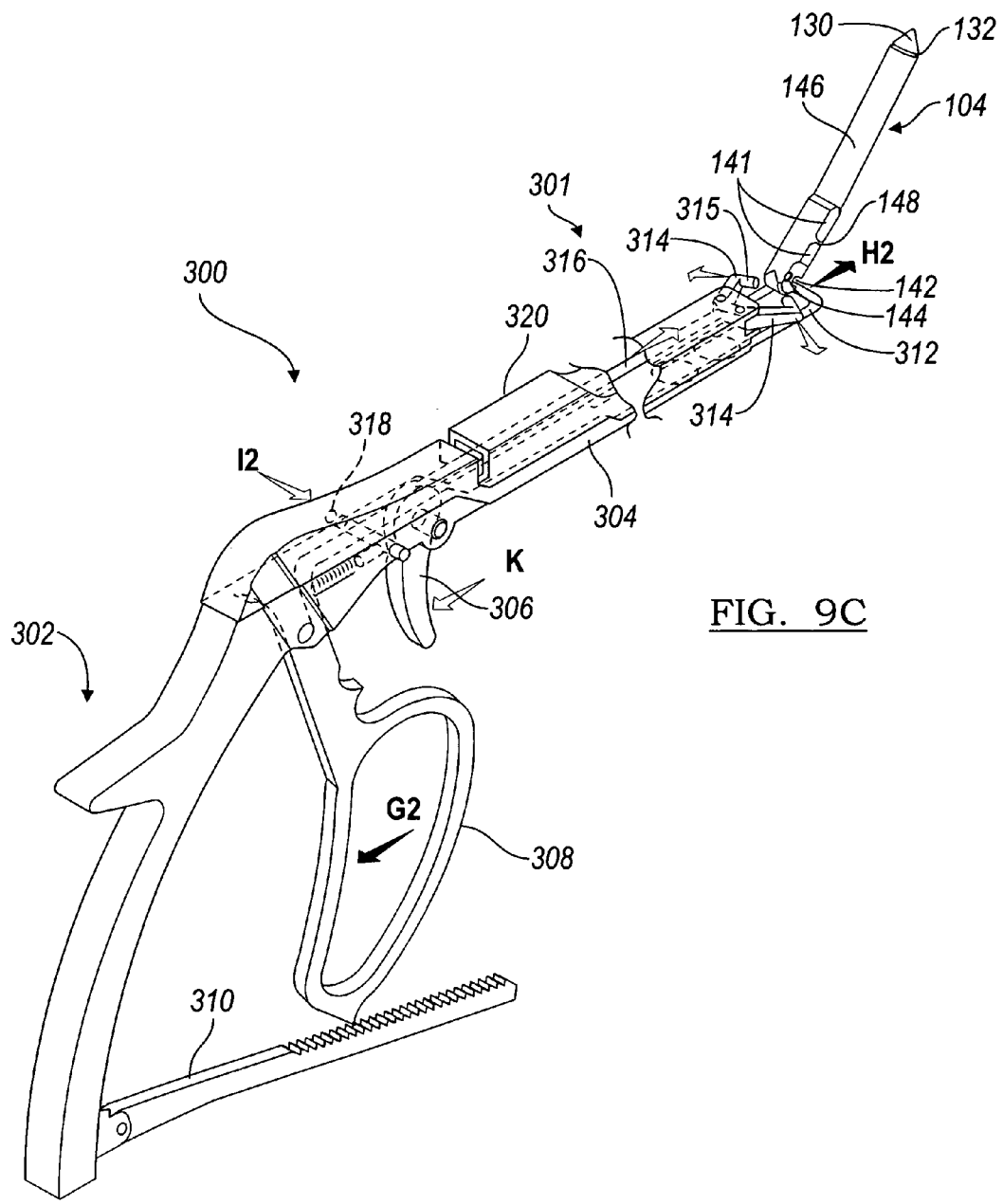
FIG. 9C is a perspective view of the percutaneous rod inserter of FIG. 9A shown with a connecting element in a second angled position.
Figure 12:
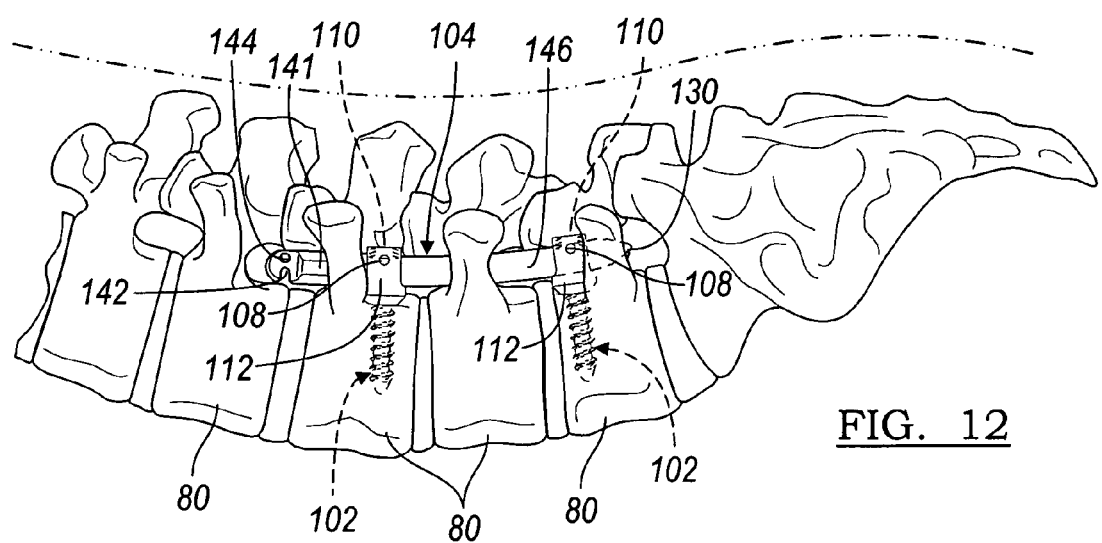
FIG. 12 is an environmental view of a connecting element and two bone fasteners implanted in a spine according to the present teachings.

The release trigger 306 can be operably coupled to a shaft 316 coupled to a pair of pivotable locking arms 314, shown in FIGS. 8A, 8B and 9A. The locking arms 314 can be biased to remain in the close position illustrated in FIG. 9B, and can be pivoted to an open position by pressing the release trigger 306 in the direction of arrow "K", as shown in FIG. 9C. The locking arms 314 can be L-shaped and have end portions 315 that can pass through a hole 144 defined in a proximal end 140 of the connecting element 104 when the locking arms 314 are in their closed position, as shown in FIGS. 8A and 9B. A safety lock 318 can be placed in the lock position indicated by arrow "I1" in FIG. 9B, to ensure that the locking arms 314 remain closed and the connecting element 104 is not released prematurely before it is properly positioned between the bone fasteners 102 as shown in FIG. 12. The connecting element 104 can be released from the rod inserter 300 by placing the safety lock 318 in the open position indicated by arrow "I2" in FIG. 9C, and pulling the release trigger 306 in the direction of the arrow K. While holding the locking arms 314 in the open position, the distal portion 312 of the angle arm 304 can be pushed out of the slot 142 of the connecting element 104.

Figure 7A:
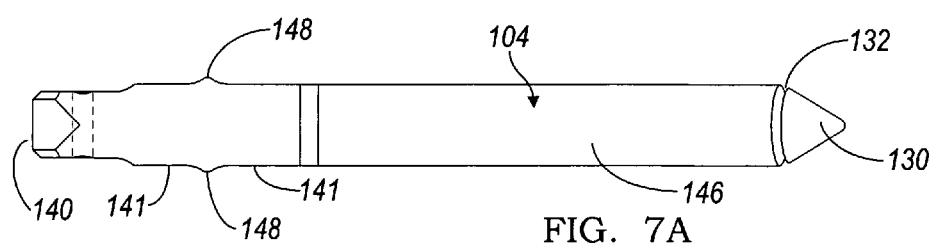
FIG. 7A is plan view of a connecting element according to the present teachings.
Figure 7B:
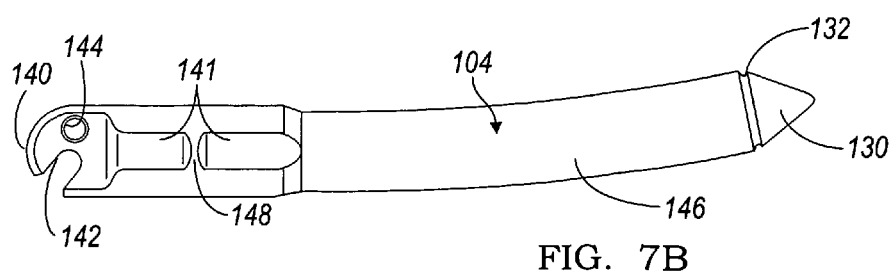
FIG. 7B is a side view of the connecting element of FIG. 7A.

Referring to FIGS. 7A and B, the connecting element 104 can include a shaft 146 having a bullet-like or rounded conical distal tip 130 for guiding insertion through tissue. A groove 132 behind the distal tip 130 can show the location of the distal tip 130 under fluoroscopy. The connecting element 104 can include two rounded protrusions 148 between flat portions 141 near the proximal end 140 for holding that portion of the connecting element 104 within the receiver portion 106 of the bone fastener 102. The shaft 146 of the connecting element 104 can have a curved portion for following the natural anatomy of the spine.

Figure 2H:
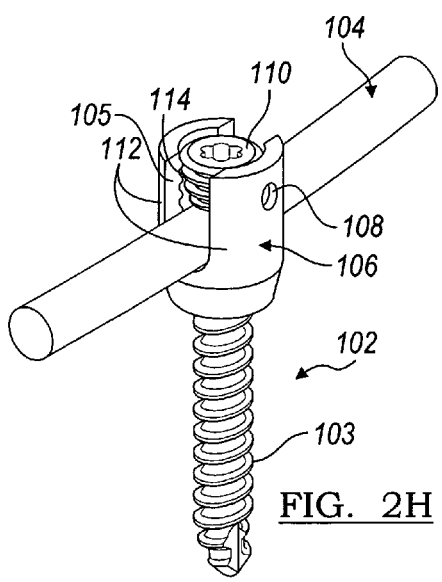
FIG. 2H is a perspective view of an exemplary bone fastener shown with a connecting element according to the present teachings.

Referring to FIGS. 2H, 11 and 11A, the bone fastener 102 can include a cannulated fastener shaft 103 that can be at least partially threaded. The shaft 103 can be received through an opening of the receiver portion 106 of the bone fastener 102. The receiver portion 106 can be U-shaped and include two arms 112 that have partially threaded inner surfaces 105. The fastener inserter 500 can be cannulated and configured to fit over a guide wire 506. The fastener inserter 500 can include an inner shaft 502 having a proximal end 510 configured to be engaged with a driver and a distal tip 504 adapted to engage with a proximal end 111 of the fastener shaft 103. The distal tip 504 can be, for example, a lobed tip, such as a pentalobe tip, or have another shape that can mate with the distal end of the fastener shaft 103. The fastener inserter 500 can also include a tubular sleeve 508 over the inner shaft 502. The tubular sleeve 508 can rotate independently of the inner shaft 502 by rotating an enlarged proximal end 514 of the tubular sleeve 508. The tubular sleeve 508 can have a threaded distal end 509 that can be threaded onto threaded inner surfaces 105 of the receiver portion 106 to secure the fastener inserter 500 to the fastener 102 and the percutaneous tower 200, as shown in FIG. 11A. The fastener inserter 500 can also include an enlarged cylindrical portion 512 that can fit into the percutaneous tower 200 and prevent the release buttons 206 from pivoting to the unlocked position (proximal ends swinging in or distal end swinging out relative to the tower 200), thus preventing release of the bone fastener 102.

The percutaneous tower 200 with the bone fastener 102 and the faster inserter 500 assembled thereon, as described above, can be advanced under fluoroscopic imaging over the guide wire 506 to implant the bone fastener 102 through the pedicle and into the vertebral body 80. The guide wire 506 and the fastener inserter 500 can then be removed and the procedure repeated to implant another bone fastener 102 into another vertebral body 80, such as an adjacent vertebral body 80. Referring to FIG. 5B, after two bone fasteners 102 have been implanted, the C/D mechanism can be attached to the percutaneous towers 200 and adjust the distance between the percutaneous towers 200 as well as the angle of the towers 200 relative to each other, and therefore relative to the spine, as discussed above. As part of the procedure, the length of the connecting element 104 and the trajectory of the connecting element 104 from cephalad to caudal or from caudal to cephalad can be determined.

Referring to FIGS. 1, 10, 2H, 9C and 9D, after the appropriate length connecting element 104 has been assembled on the percutaneous rod inserter 300, the connecting element 104 can be advanced through the first channel 210 or the second channel 212 of one of the percutaneous towers 200. Under fluoroscopic guidance, the connecting element 104 can be manipulated and gradually rotated relative to the percutaneous rod inserter 300 such that the connecting element 104 can pass through a slot of the first tower 200, such as, for example the longer slot 221 of the first tower 200 (shown in FIG. 4A). The connecting element 104 can be further manipulated with the percutaneous rod inserter 300 directionally through tissue and rotationally through further angulation/rotation relative to the rod inserter 300 until the connecting element 104 can pass through a slot of the second tower 200, such as, for example, the shorter slot 223 of the next tower 200 (shown in FIG. 4A).

The percutaneous rod inserter 300 can be configured to allow freehand manipulation of the connecting element 104 along a variable-angle path that leads through tissue from one implanted bone fastener 102 to another implanted bone fastener 102. The connecting element 104 can thus be placed into the receiver portions 106 of the bone fasteners 102. A fastener plug 110 having an external threaded portion 114 can be inserted into one of the percutaneous towers 200 and threaded into the inner surface 105 of receiver portion 106 to capture the connecting element 104 between the fastener shaft 103 and the fastener plug 110 into the receiver portion 106. The procedure can be repeated for the other percutaneous tower 200. After final compression and final tightening, distraction and angulation adjustments are made, the C/D mechanism 400, the percutaneous rod inserter 300, and the percutaneous towers 200 can be removed, as shown in FIG. 12 and closure of the percutaneous operative site can be performed according to standard protocols and procedures.

As discussed above, the present teaching can be used in connection with single level spinal fusion or other spinal procedure between two adjacent vertebrae, or between two vertebrae that are not adjacent. Further, the present teachings can be used for multiple-level procedures using more than two percutaneous towers 200 and corresponding bone fasteners 102. In this regard, the present teachings can be readily adapted to connect, for example, three or more vertebral bodies.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A percutaneous tower for the orthopedic procedures comprising:
   an outer elongated member defining a first channel and a second channel;
   a channel divider coupled to a proximal portion of the outer elongated member and selectively movable to separate the first channel from the second channel;
   an inner elongated member received within the outer elongated member;
   a release actuator operable to move the inner elongated member relative to the outer elongated member between first and second positions; and
   a fastener engagement member coupled to a distal portion of the tower and operable to engage a bone fastener when the inner elongated member is in the first position, and to disengage the bone fastener when the inner elongated member is in the second position,
   wherein the channel divider comprises two arms pivotable from a first position in which the arms do not restrict communication between the first and second channels to a second position in which the arms at least partially restrict communication between the first and second channels.

2. The tower of claim 1, wherein the fastener engagement member comprises a pair of opposing elements coupled to the distal portion of the inner elongated member and biased to protrude away from the inner elongated member when the inner elongated member is in the second position.

3. The tower of claim 2, wherein each element includes a protrusion for engaging a bone fastener when the inner elongated member is in the first position.

4. The tower of claim 1, wherein the first and second channels have first and second longitudinal axes, the second longitudinal axis being substantially parallel and transversely offset relative to the first longitudinal axis.

5. The tower of claim 4, wherein at least a portion of the second channel is defined in a proximal angled portion of the outer elongated member.

6. The tower of claim 4, further comprising first and second opposing elongated slots, each elongated slot communicating at least with the first channel.

7. The tower of claim 6, wherein the first and second elongated slots have different lengths and are structured for instrument side entry.

8. The tower of claim 1 further comprising a locking element coupled to the tower and operable to selectively lock the release actuator.

9. A percutaneous tower for the orthopedic procedures comprising:
  an outer elongated member;
  an inner elongated member received within the outer elongated member; and
  a release actuator operable to move the inner elongated member relative to the outer elongated member between first and second positions, the inner elongated member at least partially retracted relative to the outer elongated member in first position, the inner elongated member at least partially extended relative to the outer elongated member in the second position, the release actuator communicating with a proximal portion of a first channel of the tower, the release actuator including a pair of release members pivotably coupled to proximal portions of the outer and inner elongated members; and
  a locking element coupled to the tower and operable to lock the release actuator in the first position,
  wherein each of the release members defines a tool-engaging inner groove.

10. The tower of claim 9, wherein the locking element is an external ring.

11. The tower of claim 9, wherein the locking element is a tool insertable into the proximal portion of the tower.

12. The tower of claim 9, further comprising a fastener engagement member coupled to a distal portion of the inner elongated member and a distal portion of the outer elongated member and operable to engage a bone fastener when the inner elongated member is in the first position, and to disengage the bone fastener when the inner elongated member is in the second position.

13. The tower of claim 12, wherein the fastener engagement member comprises a pair of opposing elements coupled to the distal portion of the inner elongated member and biased to protrude away from the inner elongated member when the inner elongated member is in the second position.

14. The tower of claim 13, wherein each element includes a protrusion for engaging a bone fastener when the inner elongated member is in the first position.

15. A percutaneous tower for the orthopedic procedures comprising:
  an outer elongated member;
  an inner elongated member received within the outer elongated member;
  a pair of release members operable to move the inner elongated member relative to the outer elongated member between first and second positions; and
  a pair of opposing elements coupled to a distal portion of the inner elongated member, the elements biased to protrude away from the inner elongated member when the inner elongated member is in the second position, each element including a protrusion directed into the tower when the inner elongated member is in the first position,
  wherein the tower defines first and second longitudinal channels having parallel first and second longitudinal axes respectively, the second longitudinal channel defined in an angled proximal portion of the outer elongated member, and a channel divider is movably coupled to the angled proximal portion for selectively restricting at least partially communication between the first and second channels.

16. The tower of claim 15, wherein the inner elongated member is at least partially retracted relative to the outer elongated member in first position, and the inner elongated member at least partially extended relative to the outer elongated member in the second position.

17. The tower of claim 15, further comprising a locking element coupled to the tower and operable to selectively lock the release elements.

* * * * *

UNITED STATES PATENT AND TRADEMARK OFFICE
CERTIFICATE OF CORRECTION

PATENT NO. : 8,038,699 B2
APPLICATION NO. : 11/527246
DATED : October 18, 2011
INVENTOR(S) : Dan S. Cohen Page 1 of 1

It is certified that error appears in the above-identified patent and that said Letters Patent is hereby corrected as shown below:

In column 1, line 2; Insert --INTRODUCTION--

In column 1, line 51; delete second occurrence of "the release"

In column 2, line 10; After "and", delete "a"

In column 3, line 27; delete "compression-distraction", insert --compression/distraction--

In column 3, lines 29-30; delete "compression-distraction", insert --compression/distraction--

In column 4, line 8; After "is", insert --a--

In column 6, line 17; "It" should be --In--

In column 6, line 32; After "212" insert --.--

In column 6, line 45; After "Referring", insert --to-- in column 6, lines 61-62; delete "compression-distraction", insert --compression/distraction--

In column 8, line 3; "first 210" should be --first channel 210--

In column 8, line 17; "pivotable" should be --pivotably--

In column 8, line 34; "close" should be --closed--

In column 9, line 24; "faster" should be --fastener--

Signed and Sealed this
Twenty-sixth Day of June, 2012

David J. Kappos
*Director of the United States Patent and Trademark Office*